US007170034B2

(12) United States Patent
Shalev et al.

(10) Patent No.: US 7,170,034 B2
(45) Date of Patent: *Jan. 30, 2007

(54) PULSED ELECTRIC SHAVER

(75) Inventors: Pinchas Shalev, Kfar-Saba (IL); Zion Azar, Shoham (IL)

(73) Assignee: Radiancy Inc., Orangeberg, NY (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/363,365

(22) PCT Filed: Jul. 21, 2002

(86) PCT No.: PCT/IL02/00603

§ 371 (c)(1),
(2), (4) Date: Feb. 28, 2003

(87) PCT Pub. No.: WO03/009976

PCT Pub. Date: Feb. 6, 2003

(65) Prior Publication Data

US 2004/0045948 A1 Mar. 11, 2004

Related U.S. Application Data

(60) Provisional application No. 60/306,892, filed on Jul. 23, 2001, provisional application No. 60/354,019, filed on Feb. 5, 2002.

(51) Int. Cl.
*B26B 21/48* (2006.01)
*A04D 26/00* (2006.01)
*A61B 18/04* (2006.01)

(52) U.S. Cl. ...................... 219/223; 219/222; 219/223; 219/240; 219/241; 219/492; 30/140; 30/34.05; 30/29.5; 30/34.1; 606/9; 606/167

(58) Field of Classification Search ........ 219/222–223, 219/240–241, 492; 30/140, 34.05, 29.5, 30/34.1; 606/167, 27–31, 9
See application file for complete search history.

(56) References Cited

U.S. PATENT DOCUMENTS 558,465 A 4/1896 Bell
589,445 A 9/1897 Seide (Continued)

FOREIGN PATENT DOCUMENTS

BE 748225 * 8/1970 ................ 219/241

(Continued)

OTHER PUBLICATIONS

Rusting,R. L.; "Hair- Why It Grows, Why It Stops;" Jun. 2001;Scientific American; vol. 48, No. 6; pp. 56-63.

*Primary Examiner*—Robin O. Evans
*Assistant Examiner*—Stephen J. Ralis
(74) *Attorney, Agent, or Firm*—Fenster & Company

(57) ABSTRACT

A hair cutting apparatus comprising a structure (126), a portion (1216) of which being adapted for placement against a skin surface where hair is to be cut, a heat generator comprising one or more heat elements (1214) positioned to touch said hair and heated to a temperature sufficient to cut hair, at least one of said heat elements being juxtaposed with said portion and a controller that controls the power source to provide pulsed heating of said one or more heat elements.

59 Claims, 13 Drawing Sheets

U.S. PATENT DOCUMENTS

| | | | | | |
|---|---|---|---|---|---|
| 1,744,525 | A | | 1/1930 | Chase | |
| 1,926,520 | A | | 9/1933 | Fox | |
| 2,134,960 | A | | 11/1938 | Testi | |
| 2,324,148 | A | * | 7/1943 | Gravin | 30/34.05 |
| 2,727,132 | A | | 12/1955 | Hills | |
| 3,093,724 | A | | 6/1963 | Johnson | |
| 3,176,114 | A | * | 3/1965 | Kneisley | 219/223 |
| 3,197,612 | A | | 7/1965 | Reich | |
| 3,365,797 | A | | 1/1968 | Cook | |
| 3,421,216 | A | | 1/1969 | Anna | |
| 3,474,224 | A | | 10/1969 | Carter | |
| 3,521,529 | A | | 7/1970 | Strand | |
| 3,524,045 | A | | 8/1970 | Siegel | |
| 3,526,750 | A | | 9/1970 | Siegel | |
| 3,614,382 | A | | 10/1971 | Politzer | |
| 3,902,042 | A | | 8/1975 | Goldfarb et al. | |
| 3,934,115 | A | | 1/1976 | Peterson | |
| 4,051,760 | A | | 10/1977 | Glennan | |
| 4,130,955 | A | | 12/1978 | Baumgartner et al. | |
| 4,155,164 | A | * | 5/1979 | White | 433/3 |
| 4,254,324 | A | | 3/1981 | Vrtaric | |
| 4,539,467 | A | | 9/1985 | Wenger | |
| 4,608,978 | A | * | 9/1986 | Rohr | 606/9 |
| 4,617,926 | A | * | 10/1986 | Sutton | 606/9 |
| 4,745,260 | A | | 5/1988 | Albinger, Jr. et al. | |
| 4,819,669 | A | | 4/1989 | Politzer | |
| 4,940,466 | A | * | 7/1990 | Paduano et al. | 606/36 |
| 5,021,634 | A | * | 6/1991 | Santoro et al. | 219/241 |
| 5,064,993 | A | | 11/1991 | Hashimoto | |
| 5,065,515 | A | * | 11/1991 | Iderosa | 30/140 |
| 5,270,520 | A | | 12/1993 | Barzilai et al. | |
| 5,554,838 | A | * | 9/1996 | Berdich | 219/240 |
| 5,595,568 | A | * | 1/1997 | Anderson et al. | 606/9 |
| 5,606,798 | A | * | 3/1997 | Kelman | 30/41.5 |
| 5,633,003 | A | * | 5/1997 | Cantor | 424/434 |
| 5,683,380 | A | * | 11/1997 | Eckhouse et al. | 606/9 |
| 5,885,273 | A | * | 3/1999 | Eckhouse et al. | 606/9 |
| 5,968,034 | A | * | 10/1999 | Fullmer et al. | 606/9 |
| 5,993,440 | A | * | 11/1999 | Ghassemi | 606/9 |
| 6,080,146 | A | * | 6/2000 | Altshuler et al. | 606/9 |
| 6,111,222 | A | | 8/2000 | Hattori | |
| 6,187,001 | B1 | * | 2/2001 | Azar et al. | 606/9 |
| 6,228,074 | B1 | * | 5/2001 | Almeida | 606/9 |
| 6,235,015 | B1 | | 5/2001 | Mead, III et al. | |
| 6,246,027 | B1 | | 6/2001 | Griffiths | |
| 6,307,181 | B1 | | 10/2001 | Hashimoto | |
| 6,383,176 | B1 | | 5/2002 | Connors et al. | |
| 6,514,243 | B1 | * | 2/2003 | Eckhouse et al. | 606/9 |
| 6,595,985 | B1 | * | 7/2003 | Tobinick | 606/9 |
| 6,824,542 | B2 | * | 11/2004 | Jay | 606/9 |
| 6,825,445 | B2 | * | 11/2004 | Shalev et al. | 219/223 |
| 2002/0004986 | A1 | | 1/2002 | Furst et al. | |
| 2004/0098863 | A1 | | 5/2004 | Shalev | |

FOREIGN PATENT DOCUMENTS

| | | | |
|---|---|---|---|
| DE | 3406966 | * | 8/1985 |
| EP | 0 102 289 | | 3/1984 |
| EP | 0 736 308 | | 10/1996 |
| EP | 0 788 814 | | 6/1997 |
| EP | 1 269 881 | | 1/2003 |
| FR | 2 531 655 | | 2/1984 |
| FR | 2 612 381 | | 9/1988 |
| GB | 658068 | | 10/1951 |
| IT | 1 201 364 | | 1/1989 |
| IT | 1201364 | * | 1/1989 |
| JP | 1-288291 | * | 11/1989 |
| JP | 5-228016 | | 9/1993 |
| JP | 8-223783 | | 8/1996 |
| WO | WO 82/03520 | | 10/1982 |
| WO | WO 99/19123 | | 4/1999 |
| WO | WO 03/009976 | | 2/2003 |

* cited by examiner

PULSED ELECTRIC SHAVER

RELATED APPLICATIONS

The present application is a U.S. national application of PCT/IL02/00603, filed on Jul. 21, 2002. The present application claims the benefit under §119(e) of U.S. provisional application No. 60/306,892 filed on Jul. 23, 2001, and U.S. provisional application No. 60/354,019 filed on Feb. 5, 2002, the disclosures of which are incorporated herein by reference.

FIELD OF THE INVENTION

The present invention relates to removing hair with periodically applied heat without damaging the skin.

BACKGROUND OF THE INVENTION

The removal of unwanted hair from the body can be accomplished with non-mechanized means, for example razors, tweezers or wax, all of which are uncomfortable to use, irritate the skin and/or cause damage to the skin.

Mechanized cutting means for cutting hair, for example dry shavers, in addition to being uncomfortable to use, are limited to cutting hair of a specific length. Beard trimmers, for example, cut facial hair stubble, but cannot cut longer hairs on the scalp.

Alternate devices that use an electrical or electromagnetic source, for example electrolysis and photothermolysis, are effective but usually require an experienced operator to ensure proper administration without untoward side effects.

The use of heated wires or other structures to cut hair from a skin surface has been proposed. However, a heat generator that generates heat of a sufficient magnitude to cut hair and that cuts the hair close to the skin, often damages the skin. Alternatively, since the heat generator is offset from the skin to prevent skin damage, unwanted stubble is left behind.

In Peterson, U.S. Pat. No. 3,934,115, parallel metal strips on the upper side of a ceramic facing that contacts the skin, are used to cut hair. Hills, in U.S. Pat. No. 2,727,132 and P. Massimo in IT 1201364, use a continuously heated element to burn hair. P. M. Bell in U.S. Pat. No. 558,465, D. Seide in U.S. Pat. No. 589,445, G. S. Hills in U.S. Pat. No. 2,727,132, G. L. Johnson in U.S. Pat. No. 3,093,724, Hashimoto in U.S. Pat. Nos. 5,064,993 and 6,307,181 B1, F. Solvinto in FR 2531655 and EP 0102289, and E. Michit in FR 2612381, use a continuously heated wire to burn hair. J. F. Carter in U.S. Pat. No. 3,474,224, provides a circular comb device for burning nose hairs. Aside from physically separating the skin from the heated element, these references do not appear to provide other protection against burning of the skin.

Vrtaric in U.S. Pat. No. 4,254,324, provides a heat hair cutting system that is applied only to the tips of the hair to remove the split ends.

A prior art system for depilation, based upon photothermolysis is shown in U.S. Pat. No. 6,187,001, the disclosure of which is incorporated by reference. In this method, radiant energy is used to heat the air surrounding the skin to remove hair. EP publications EP 0 736 308 and EP 0 788 814, the disclosures of which are incorporated herein by reference, utilize radiant energy to selectively heat the hair, destroying it.

SUMMARY OF THE INVENTION

According to an aspect of some embodiments of the present invention, pulsed heat is applied through a heat generator containing one or more heat elements that contact the skin at least intermittently. In an exemplary embodiment, a pulsed heat generator provides pulsed heat at the heat elements wherein the pulses of heat are short enough so that although the temperature is high, the amount of heat transferred to the skin does not damage the skin. On the other hand, hair that contacts the heat element is destroyed, due to the lower heat capacity of the hair. Such a device may contact the skin substantially continuously.

According to an aspect of some embodiments of the present invention, a device comprises a heat generator that generates continuous heat of sufficient temperature to cut hair while contacting the skin. However, during the process of cutting hair, the heat generator is prevented from damaging the skin by controlling the period of time during which heat continuously contacts a given area of skin. In some embodiments of the present invention, a heat generator continually contacts the skin and the period of its heat generation is limited to prevent skin damage. In some embodiments of the present invention, the generator remains hot throughout its duty cycle and is removed from contacting a section of skin to limit the period of time in which heat is applied, thereby preventing skin damage.

As used herein, a heat generator is defined as a unit containing one or more heat elements heated to a temperature sufficient to cut hair during a given period of time in which it is in contact with the hair. It should be understood that current applied to the heat element at the line frequency (50–60 Hz) is to be considered continuous current, since it provides substantially constant heat.

Unless specified, further embodiments apply to both pulsed heating aspects and non-pulsed heating aspects of the present invention. Furthermore, while either pulsed or continuous heating may be described in reference to an embodiment of the invention, pulsed heating is generally usable in all the embodiments that are described with continuous heating. Additionally, embodiments that are described as using pulsed heating can use continuous heating if means for avoiding overheating of the skin as described herein are provided.

The cutting of a hair is dependent upon the magnitude of heat absorbed by the hair, whether a low temperature over a long period of time or a high temperature over a short period of time, whether pulsed or non-pulsed heat. Hence, the heat generator may generate heat at a lower temperature for a longer period of time or at a higher temperature for a shorter period of time in order to cut hair.

Heat builds in a specific area of a given hair and reaches a sufficient magnitude to cut the hair substantially independent of the hair length. In an exemplary embodiment of the present invention, a single apparatus cuts hair of a variety of lengths, from facial stubble to long hair on the scalp, in a variety of persons. Additionally or alternatively, the present invention allows a single apparatus to cut hair of a variety of lengths without exchanging, for example, cutter accessories. Further, the heat element used to cut hair, provides a sterile cutting environment, preventing the transmittal, for example, of scalp bacteria from one user to the next.

In some embodiments of the present invention, a heat generator provides heat of sufficient temperature to cause cessation of hair regrowth through destroying a hair growth regulatory mechanism as identified by R. L. Rusting in "Hair—Why it grows, Why it stops", *Scientific American*

248:6 June 2001, pp. 56–63. Alternatively, a heat generator provides heat at a lower magnitude to cause delay of hair regrowth through partial destruction of the hair growth regulatory mechanism.

In an exemplary embodiment of the invention, the heat generator contains one or more heat elements, for example a heated wire and/or heated strip that contacts the hair and, optionally, the skin. Additionally or alternatively, the one or more heat elements consist of one or more of a wire, a ribbon, or a conductive coating on a non-conductive surface, for example a ceramic material in the form of a bar. Optionally, the one or more heat elements contain, at least in part, a metal. Alternatively, they do not contain any metal.

In other embodiments of the invention, the heat generator comprises two or more heat elements. The hair is cut, for example, with absorption of an appropriate amount of cumulative heat by each hair. Two or more heat elements promote faster transfer of the necessary cumulative heat than, for example one heat element, allowing faster movement of the unit while cutting the hair.

Additionally or alternatively, two or more heat elements allow each heat element in the heat generator to maintain a lower temperature while cutting hair as compared to a heat generator with a single heat element at a higher temperature.

Additionally or alternatively, the pulsed current is pulsed at different times through the two or more heat elements and is, for example, synchronized so that one heat element generates heat while another heat element does not generate heat or, optionally, generates heat at a lower temperature.

Optionally, the heat generator comprises one or more walls that are perpendicular to the skin comprising, for example, a slot through which hair passes. In an exemplary embodiment, the one or more heat elements are moved by the device in relationship to the slot during use to prevent damage from heat buildup in a given area of skin. For example, in some embodiments of the invention, the heat generator, or a portion of the heat generator, is mechanized to be periodically removed from an area of skin. The heat generator, for example lifts the one or more heat elements from the skin in a regular cycle or by moving them along the surface of the skin. When a mechanized heat generator contains two or more heat elements, the heat elements, for example, have an axis parallel to the skin and rotate around the axis that is parallel to the skin.

In an alternative mechanical embodiment, the mechanization provides for rotation of the heat elements about an axis perpendicular to the skin, such that the heat element moves along the surface of the skin. This provides for contact times with the skin that do not cause skin burns while providing for continuous cutting action, since all of the heat elements are adjacent to the skin with a high duty factor.

In some embodiments of the present invention, two or more heat elements are situated on a vertical plane in relationship to the skin surface, so that the hairs are cut successively closer to the skin as the heat elements sequentially pass an area of skin. Alternatively or additionally, the heat generator comprises two or more heat elements situated on a horizontal plane to the skin so that cumulative heat appropriate for cutting a hair may be provided sequentially as the multiple heat elements pass the same site.

In an exemplary embodiment, the heat generator comprises two or more heat elements of different cross sectional sizes, with the heat element of greater cross section providing greater transfer of heat to cut hair while at the same temperature as the heat element of lesser cross section. Optionally, heat elements of different cross sectional sizes are located in a cylinder about an axis that moves perpendicular to the skin. Additionally or alternatively, the heat elements of different cross sectional sizes are situated in a non-vertical plane in relationship to the skin with one heat element at a different height from the skin than another heat element. For example the thicker heat element is located further from the skin to provide faster coarse cutting of the hair. Additionally or alternatively, the heat elements of different cross sectional sizes are situated on a horizontal plane in relation to the skin with one behind the other. For example, the thicker heat element is located in front of the thinner heat element, so the thinner heat element is used to cut the relatively fewer hairs that may have been left uncut the larger first heat element.

Similarly, heat elements of different cross sectional sizes that are arranged in a cylinder or on a horizontal or non-horizontal plane, allow the thicker heat element to cut the bulk of the hairs in its path while the thinner heat element cuts the relatively few hairs missed by the first heat element.

In an exemplary embodiment, the heat generator cuts hair in conjunction with a cooling apparatus, for example a fan, to provide cooling to the skin during the cutting process. In addition, when pulsed heating is used, the fan helps to remove heat from the heat element during the "off" time, so that a higher repetition rate for the heat pulses and a higher duty cycle can be used.

In an exemplary embodiment, the hair cutting apparatus includes a grasping structure designed to be grasped by an operator to which the heat generator is attached. The heat generator is held by the grasping structure at a specific angle to the skin, for example, perpendicular to the skin. Optionally, the heat generator is held at a non-perpendicular angle to the skin. The angle of heat generator, whether perpendicular or non-perpendicular is varied, for example, according to the design of the grasper.

In an exemplary embodiment, one or more posts provide the connection between the grasping structure and the heat generator. These posts are, for example, flexible or spring loaded so that as the heat generator moves across the contour of the skin, the heat generator moves up and down and/or swivels on the flexible posts in relation to the grasper. This movement prevents, for example, the heat element from pressing with undue force into the skin surface, causing skin damage.

In an exemplary embodiment of the present invention, heat is applied through a heat element that contacts the skin while two or more skin depressors located in proximity to the heat elements hold the skin flat. The two or more skin depressors prevent the heat element from sinking into the skin and causing skin damage due to increased contact area between the skin and the heat element. Optionally, one or more rows of skin depressors touch the skin and the one or more heat elements are parallel to the one or more rows of skin depressors. Additionally or alternatively, two rows of skin depressors are provided and the one or more heat elements are located between the two rows of skin depressors, optionally parallel to the two rows of skin depressors. Optionally, the one or more heat elements are not parallel to the two rows of skin depressors.

In an exemplary embodiment, the one or more heat elements of the heat generator are held at one or both ends by a tension generator. The one or more tension generators comprise, for example, a spring-loaded mechanism, to tighten the one or more heat elements of the heat generator during longitudinal expansion that may occur during heat generation. Additionally or alternatively, said one or more tension generators tighten the one or more heat elements to prevent substantial deformation while pressing against hair during hair cutting.

In an exemplary embodiment of the present invention, the one or more skin depressors are designed so that the one or more tension generators do not cause skin damage during cutting. For example, the one or more skin depressors located near the tension generator protrude beyond the tension generator so the skin does not contact the tension generator, thereby preventing buildup of heat and resultant skin damage.

Additionally or alternatively, the one or more rows of skin depressors provide a cooling mechanism for the heat elements. As the pressure on the heat elements of the heat generator, caused by the hairs in its path, increases, the heat elements of the heat generator displace and touch one or more of the skin depressors and cool. This cooling of the heat elements of the heat generator prevents heat buildup that can cause damage to the skin. A second pass cuts the hairs in the path of the cooled heat generator that were not cut during a first pass.

Optionally, the one or more rows of skin depressors provide current to the one or more heat elements of the heat generator only when the heat generator is in motion. In an exemplary embodiment the heat elements contain, for example, a positive charge potential and the two or more rows of skin depressors are connected to an electrical ground. As the heat generator is moved along the skin and comes against hairs in its path, the cool heat elements remain stationary against the hairs. As the heat generator continues motion, the heat elements bend and touch a row of skin depressors, thereby completing the circuit so electricity flows through the heat elements to the grounded skin depressors and the elements heat up. Upon cessation of motion, the heat elements no longer press against hairs in their path and become straight, for example with the assistance of the tension generated by the tension generator, so they no longer touch a row of skin depressors. The current through the heat elements is thereby disrupted and the heat elements cool.

In an exemplary embodiment, heat is applied through a heat element controlled by a motion detector so the heat element provides heat only while the heat element moves in relation to the skin. Upon slowing of the heat generator's motion below a specific rate, or its cessation of motion, the motion detector stops the production of heat by the heat element. Additionally or alternatively, in response to reduction or cessation of motion, the temperature of heat, produced by the heat generator, is reduced.

In an exemplary embodiment, the temperature and (when a pulsed heat source is used) pulse rate, and/or pulse width in a single heat element is controlled by a velocity detector. One or more of these factors is raised or lowered responsive to the velocity of the heat generator. This control, for example, prevents damage to the skin by excessive heat at a lower velocity. Additionally or alternatively, a velocity detector controls one or more factors of temperature, pulse rate and/or pulse width in each heat element individually when there are, for example, two or more heat elements.

In an embodiment of the pulsed aspect of the present invention, the pulsed heat generator applies continuous current as it moves at a higher speed in relation to the skin and applies pulsed current optionally at a rate that is reduced as the heat generator moves at a lower speed.

There is thus provided a hair cutting apparatus comprising a structure, a portion of which being adapted for placement against a skin surface where hair is to be cut a heat generator comprising one or more heat elements positioned to touch said hair and heated to a temperature sufficient to cut hair, at least one of said heat elements being juxtaposed with said portion and a controller that controls the power source to provide pulsed heating of said one or more heat elements. Optionally, the one or more heat elements are heated for a period of between 10 and 100 msec for each on-off cycle. Optionally, the heating of the heat element is repeated at a pulse repetition rate of 1–100 Hz.

In an exemplary embodiment, said controller comprises a velocity detector. Optionally, the velocity detector causes said heat generator to increase its rate of repeated pulsing when the velocity of said apparatus increases in relation to said skin and to decrease its rate of repeated pulsing when the velocity of said apparatus decreases in relation to said skin.

Optionally, the velocity detector causes said heat generator to increase the width of each pulsation during said repeated pulsing when the velocity of said apparatus increases in relation to said skin and to decrease the width of each pulsation during said repeated pulsing when the velocity of said apparatus decreases in relation to said skin. In an exemplary embodiment, said pulsation changes to continuous heating when the velocity increases above a specific rate, as sensed by said velocity detector.

Optionally, the velocity detector causes said heat generator to increase the temperature of said heat element when the velocity of said apparatus increases in relation to said skin and to decrease the temperature of said heat element when the velocity of said apparatus decreases in relation to said skin. Optionally, said velocity detector comprises an optical velocity detector. In an exemplary embodiment, said velocity detector comprises a mechanical velocity detector.

In an exemplary embodiment, the heat generator includes an interruptible power supply that energizes said heat element, said controller controls the interruptible power supply to periodically heat said heat generator to a temperature at which it is hot enough to cut hair and then causes it to cool to a lower temperature at which said skin surface is not damaged.

Optionally, said controller comprises a motion detector. Optionally, the motion detector controls said heat generator, switching said heat generator on when said heat generator is in motion in relation to said skin and switching said heat generator off when said heat generator is not in motion in relation to said skin. Alternatively, said motion detector comprises an optical motion detector. Optionally, said motion detector comprises a mechanical motion detector.

In an exemplary embodiment, the one or more heat elements comprise ribbon-shaped and a wide side of said ribbon-shaped heat elements are substantially perpendicular to said skin. Optionally, the one or more heat elements comprise a wire substantially parallel to said skin. Optionally, the one or more heat elements comprise two or more heat elements. Additionally or alternatively, a plane formed by the two or more heat elements is parallel to said skin. Optionally, the plane formed by the two or more heat elements is perpendicular to said skin. Optionally, the plane formed by the two or more heat elements is neither parallel nor perpendicular to said skin.

In an exemplary embodiment, the two or more heat elements have different cross-sectional areas. Optionally, the two or more heat elements have different cross-sectional configurations. Optionally, the heat applied by at least two of the two or more heat elements is applied at a different pulse rate. Optionally, the heat applied by at least two of the two or more heat elements is applied at a different pulse width or the temperature in at least two of the two or more heat elements is different.

In an exemplary embodiment of the present invention, at least one end of one heat element is attached to a tension generator. Optionally, the tension generator comprises a spring. Optionally, the tension generator comprises a spring-loaded wire. Additionally or alternatively, said portion that is adapted for placement against the skin comprises two or more skin depressors that contact said skin surface. Optionally said two or more skin depressors are perpendicular to said skin.

Optionally, said two or more skin depressors comprise one or more rows of skin depressing elements.

In an exemplary embodiment, said two or more skin depressors comprise at least two rows of skin depressing elements. Optionally, said two or more skin depressors comprise two parallel rows of skin depressing elements. Optionally, said one or more heat elements are located between said two rows of skin depressing elements.

Additionally or alternatively, at least one heat element is parallel to one or more rows of skin depressing elements. Optionally, said at least one heat element is not parallel to one or more rows of skin depressing elements. Alternatively, said at least one heat element is not parallel to said two or more rows of skin depressing elements. Optionally, at least one end of one heat element is connected to a tension generator and one or more of said skin depressing elements protrude beyond said tension generator.

In an exemplary embodiment, when the at least one heat element is so constructed that when it contacts one or more hairs during motion, it displaces opposite its direction of motion in relation to the skin. Optionally, when said heat element displaces in an amount sufficient to contact one of said skin depressors, it cools as it contacts the skin depressors. Optionally, when said heat element displaces in an amount sufficient to contact one of said skin depressors, it heats as it contacts the skin depressors.

In an exemplary embodiment, said portion adapted for placement against a skin surface is separate from said structure and said portion is mounted with one or more mountings on said structure. Optionally, said mounting comprises flexible posts. Additionally or alternatively, said mounting comprises spring-loaded mountings. Additionally or alternatively, said mountings are electrically connected to said heat elements.

In an exemplary embodiment, the controller comprises a motor that moves the heat elements along the skin, so that the temperature of the skin does not rise to a level, that causes it to burn. Optionally, the heat elements are elongate heat elements arranged to form a discontinuous cylindrical surface having a rotation axis. Additionally or alternatively the heat elements rotate about the axis they are periodically brought into contact with and removed from contacting said skin surface. Optionally, the axes of the heat elements radiate from an axis, said axis being perpendicular to the axes of the heat elements. Optionally, the controller rotates the elongate heat elements about the axis.

In an exemplary embodiment, said apparatus includes a fan that provides cooling for at least one heat element.

There is thus further provided a method of cutting hair comprising providing a pulsatingly heat element touching the skin, said heat element being heated to a peak temperature high enough to cause the cutting of hair without burning of skin at said position, wherein said pulsation allows the heat element to cool between pulses to an extent that it does not burn the skin while still cutting hair.

Optionally, said reducing comprises reducing the pulsation rate of pulsated heat to the heat element. Optionally, reducing comprises reducing the width of each pulsation of pulsated heat to the heat element. Additionally or alternatively, reducing comprises reducing the temperature of each pulsation of pulsated heat to the heat element. Alternatively, reducing is accomplished by a velocity detector when it detects a reduction in velocity of said heat element in relation to said skin.

BRIEF DESCRIPTION OF THE DRAWINGS

Exemplary non-limiting embodiments of the invention are described in the following description, read with reference to the figures attached hereto. In the figures, identical and similar structures, heat elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DESCRIPTION OF EXEMPLARY EMBODIMENTS

Figure 1:
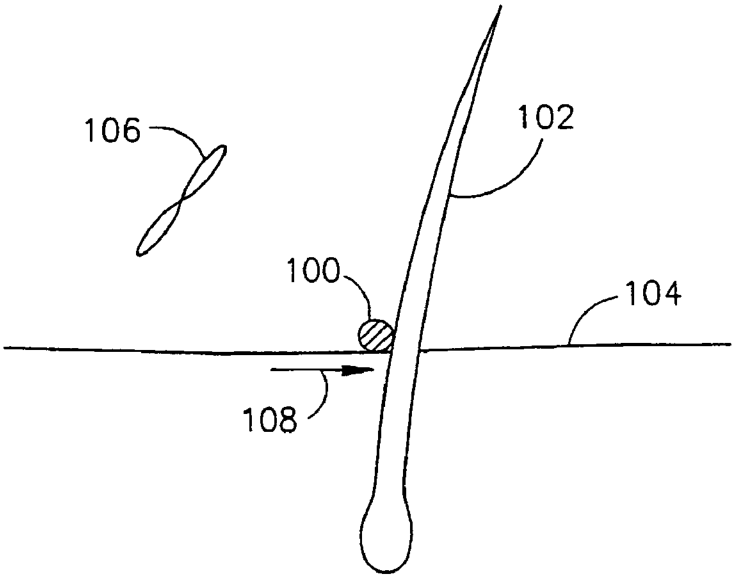
FIG. 1 is a simplified schematic diagram of a wire cutting a hair, in accordance with an exemplary embodiment of the invention.

FIG. 1 is a schematic cross-sectional diagram of an embodiment of a wire 100 cutting a hair 102, while optionally touching a portion of skin 104, in accordance with an exemplary embodiment of the invention.

In a pulsed embodiment of the invention, the current through wire 100 is pulsed on for between 10 and 100 milliseconds. The length of current pulse, for example, is based upon the peak temperature of wire 100, for example, or other factors such as the speed at which wire 100 passes over skin 104. During this short period of time, wire 100 heats to the desired temperature. However, in the short time that the current is on, the amount of heat generated is not sufficient to heat skin 104 to a temperature at which it is damaged. Because the heat dissipates in skin 104 faster than in a hair, wire 100 does not have sufficient time to damage skin 104, but cuts hair 102. Generally, wire 100 moves in a direction 108 along a portion of skin 104 and if the movement is halted, absent the pulsing of the heat, wire 100 will burn skin 104

In non-pulsed embodiments of the present invention, for example, wire 100 is periodically removed from skin 104 to prevent skin damage. Additionally or alternatively, wire 100 remains in constant contact with skin 104 and the current through wire 100 is turned off to prevent skin damage when wire 100 is stationary with respect to skin 104. Mechanisms, for example, that turn the current to wire 100 on or off while in contact with skin 104 or periodically remove wire 100 from skin 104, will be explained below.

In an exemplary embodiment, the current through wire 100 is 0.5 A, though it may vary, depending on the dimensions and/or materials of wire 100. In order to cut efficiently, wire 100, for example, reaches a peak temperature of between 700 and 800° C., when wire 100 is held against hair 102 for 10–50 milliseconds. Lower temperatures, for example 500° C., can be used to cut hair 108 when wire 100 is held against hair for longer periods of times, for example, 50–100 milliseconds. Higher temperatures, for example 1000° C., can be used to cut hair 108 when wire 100 is held against hair 108 for shorter periods of time, for example, 5–10 milliseconds.

Optionally, a fan 106 is provided that cools skin 104 and wire 100 to avoid overheating skin 104. The operating temperature of the device and/or the duration of heat application to a given area of skin 104 will likely change based upon whether or not a fan is used in conjunction with wire 100. For example, temperatures of 1000° C. for a duration of more than 10 milliseconds are contemplated for cutting hair 108 in conjunction with fan 106.

Additionally or alternatively, the color of wire 100 as it attains different temperatures, may be used as a determinate of hair cutting ability. For example, the power supply may be set to a level that causes wire 100 to become red hot at which it will cut hair 108 rapidly. Additionally or alternatively, the power supply may be set to a level that causes wire 100 to become yellow to yellow-red hot or a color indicating a temperature at which, for example, it will cut hair 108 less rapidly. Optionally, an operator can be apprised of these temperature-associated colors. By increasing and/or decreasing a current control to wire 100, for example, the operator can cause wire 100 to glow at a specific color, indicating that an optimal temperature of wire 100 has been reached.

In an exemplary embodiment, wire 100 has a diameter of 0.070 millimeters, 0.01 millimeters or less, for example, when manufactured of a flexible material. A flexible material, for example, comprises, for example, a wire 100 manufactured from Kantaal D, (an alloy of nickel chromium and other metals manufactured by Kantaal Group). Alternative materials for wire 100 include Nichrome or other wire resistance materials. Alternatively, wire 100 could have a diameter of between 0.08 and 0.5 millimeters, when a less flexible material is used for its manufacture.

In an exemplary embodiment, wire 100 has a length, for example, of 10 millimeters, so that it cuts only a 10-millimeter swath of hair on each pass. Optionally, wire 100 has a longer length, for example 30 millimeters or more, providing a larger swath of hair cut with each pass.

An advantage of the present invention over prior art dry shavers, for example, is that heated wire 100 sterilizes skin surface 104, or provides an aseptic environment, during cutting hair 108. Additionally or alternatively, the heat of wire 100 suppresses and/or does not promote the spread of bacteria or other unwanted organisms during the cutting process. In contrast, for example, a dry shaver neither provides an aseptic environment nor suppresses the spread of bacteria during the cutting process. Hence, bacteria is often spread on skin 104 during cutting with a dry shaver, with a resultant infection, for example, when skin surface 104 is breached.

Figure 2:
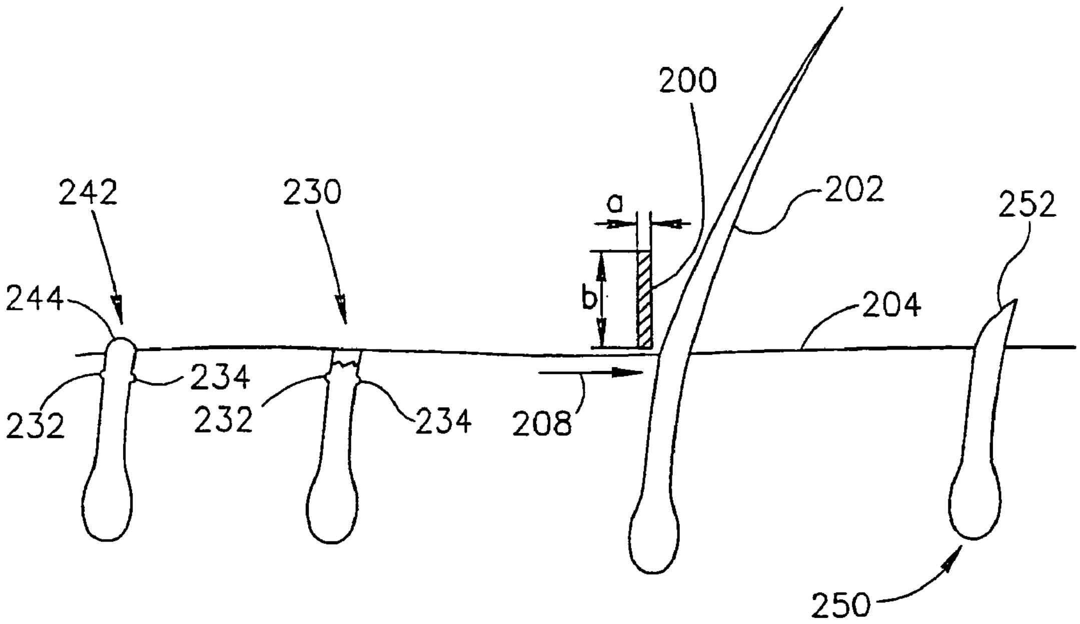
FIG. 2 is a simplified electrical schematic diagram of strip cutting a hair, in accordance with an exemplary embodiment of the invention.

FIG. 2 is a schematic diagram of an alternative embodiment of a hair cutting device utilizing a ribbon 200, shown in cross section (optionally touching the skin), cutting a hair 202 while moving in a direction 208 along a skin surface 204, in accordance with an exemplary embodiment of the invention. A follicle 232, the remains of a cut hair 230, is, for example, cut below skin surface 204.

R. L. Rusting in "Hair—Why it grows, Why it stops" by, *Scientific American* 248:6 June 2001, pages 56–63, identifies the existence of stem cells within a bulge 234 that are part of the hair regulatory mechanism. In an exemplary embodiment, the heat of ribbon 200 radiates from skin surface 204 through hair follicle 232 to affect the cells of bulge 234, thus providing a cessation of hair regrowth for a period of time, for example, a few days, a few weeks, a few months or even permanently.

In an exemplary embodiment of the present invention, a curved end 244 forms on a hair bulb 242 that has been cut with a heat element, for example ribbon 200, that is more comfortable to shaved skin 204. This is a distinct advantage over, for example most razors and electric shavers, that often leave a hair bulb 250 with a sharp point 252 that is uncomfortable to shaved skin 204.

Ribbon 200, for example, has a width, dimension a, of 0.05 millimeters or less, when manufactured from strong materials and/or the peak temperature is low. Alternatively, ribbon 200 could have a higher width dimension a, for example 0.2 millimeters or more, when manufactured from weaker materials and/or a higher peak temperature is maintained. Height, a dimension b, is not critical, except that excessive height results in high power consumption.

Ribbon 200 with a greater height dimension b, however, allows a large heated area to contact hair 202, providing faster buildup of heat in hair 202 and faster rate of cutting. A narrow width dimension a, provides less heat transfer to skin 204 when using a ribbon 200 with a greater height b for rapid cutting. Other useful shapes, for example a sharp edge on the lower portion of ribbon 200 or an oval shape to ribbon 200, provide other associated advantages as will be clear to persons of skill in the art.

In general the dimensions of ribbon 200 can be based on the amount of power available (whether the device run from batteries or from mains), and factors including whether the heat is pulsed or continuous, whether movement of ribbon 200 is mechanical or manual, whether fan cooling is provided and limitations on the heat capacity of the ribbon 200 so that skin damage is avoided. The values given above are typical for the particular material and are not to be considered as limiting.

Figure 3:
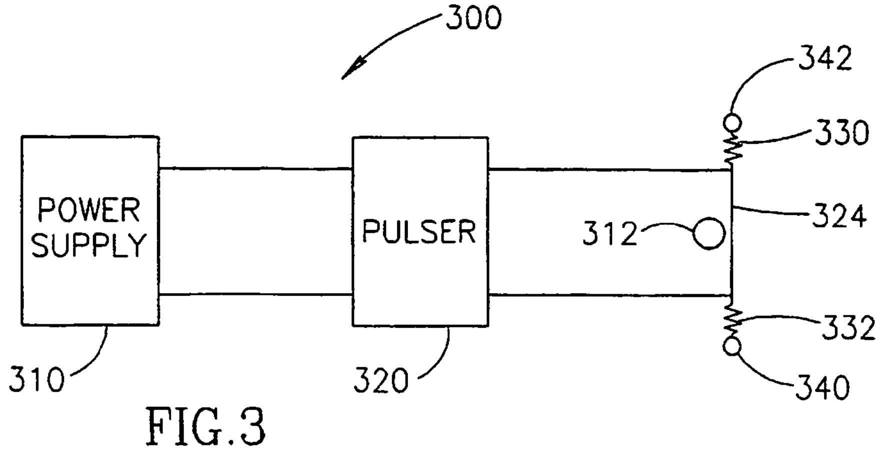
FIG. 3 is a simplified schematic diagram, in accordance with an exemplary embodiment of the invention.

FIG. 3 is a simplified schematic representation of an embodiment of a device 300, in accordance with an exemplary embodiment of the invention. A power supply 310, for example, produces between 3 and 30 volts and between 0.030 and 5 amperes, depending on the dimensions of a heat element 324. Power from power supply 310 causes heat element 324 to heat to a temperature that is sufficient to cut hair, for example, between 700–800° C. when contact with a hair is between 10 and 50 milliseconds. An optional pulsar 320 (which can be part of power supply 310) regulates the current produced by power supply 310 so that it, for example, produces pulsed heat for a period of 10–200 milliseconds such as 50 ms. The time between pulses is regulated, depending on the rest of the construction, to allow heat element 324 to cool sufficiently and to be off for a sufficient period to avoid burning of the skin and build-up of heat, even if heat element 324 is not moved. Generally, the pulse rate is between 1 and 100 Hz. However, as described below, if mechanical motion is provided to heat element 324 so that it does not continuously contact the skin, high duty cycles and even continuous heating may be provided.

Heat element 324 is optionally attached to a post 340 by a spring 332 and to a post 342 by a spring 330. These springs maintain tension on heat element 324 even as it expands during the heating phase so that it remains taut against a hair 312, shown in cross section.

Figure 4A:
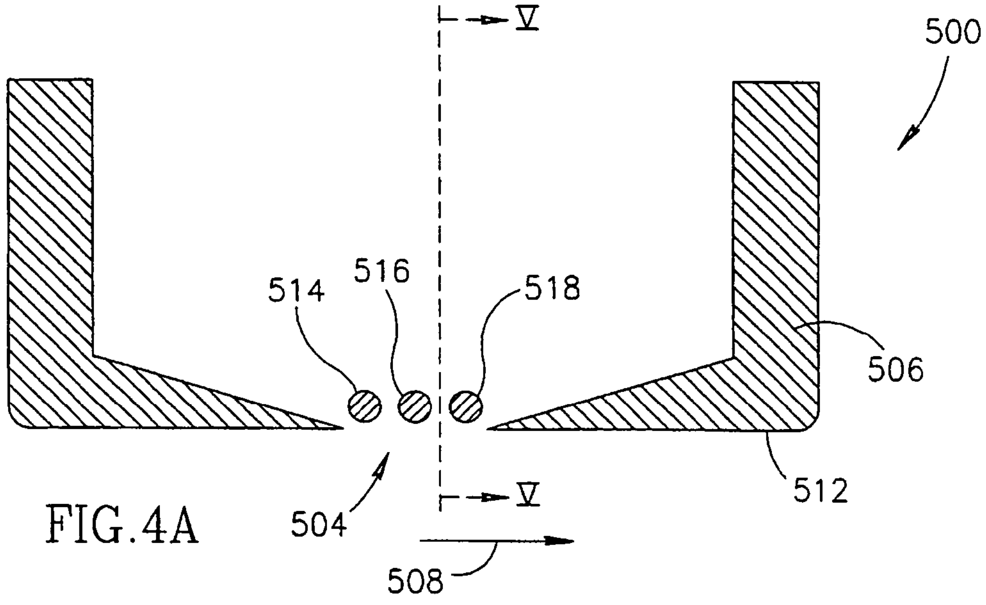
FIGS. 4A and 5 are respective orthogonal cross-sectional views of a hair cutting apparatus, in accordance with an exemplary embodiment of the invention.
Figure 5:
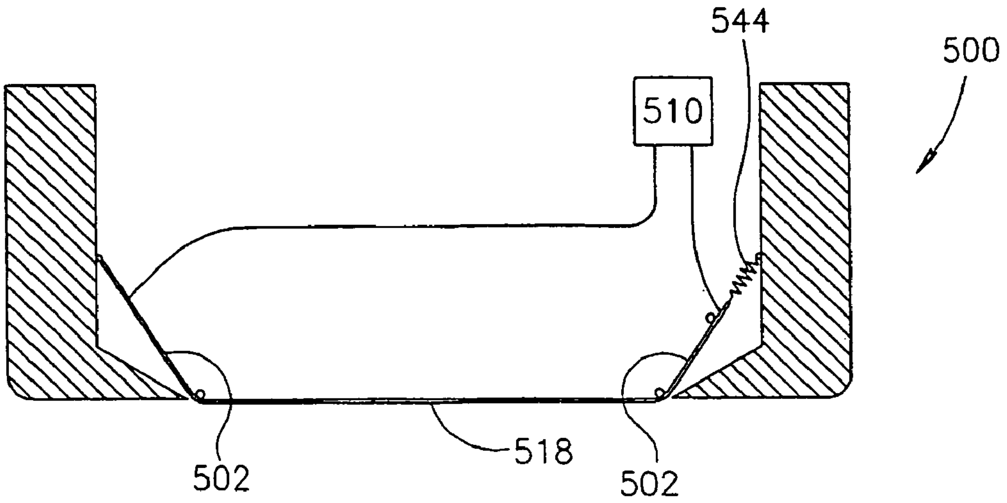

FIGS. 4A and 5 are respective orthogonal cross-sectional views of a hair cutting apparatus 500, with FIG. 5 taken along lines V—V of FIG. 4A, in accordance with an exemplary embodiment of the invention. Apparatus 500 comprises one or more heat elements 514, 516 and 518 stretched across a slot 504 in a housing 506. Slot 504 is, for example, 1.0 centimeter wide to allow a small swath of hair to enter slot 504 for cutting. Alternatively, slot 504 may have a width of 0.5 centimeters or less, to cut an even smaller swath of hair or a width of 2.0 centimeters of more in order to cut a larger swath of hair on each pass.

Heat elements 514, 516 and 518, as shown in FIG. 4A, are on the same horizontal plane so that they are all, for example, in continuous contact with a portion of skin 524. Additionally or alternatively, the heights of heat elements 514, 516 and 518 can be set so that, for example, they are not in contact with skin 524 and cut hairs to a specific length. Alternatively or additionally, heat elements 514, 516 and/or 518 can have different duty cycles, limiting, for example, the number of heat elements 514, 516 and/or 518 providing heat at any given time.

A spring 544 (FIG. 5) is attached to each heat element 518 (only 518 is shown in FIG. 5) to keep it taut even as it expands during heating. Heat element 518 is attached to a power supply 510, shown schematically. One way of placing heat element 518 so it contacts skin 524 is to provide rods 502, mounted in walls 506 that are attached to heat element 518 and bring heat element 518 close to skin surface 524. When heat element 518 is formed in a ribbon, for example, slots may be placed in rods 502 to position and orient ribbon heat element 518.

Figure 4B:
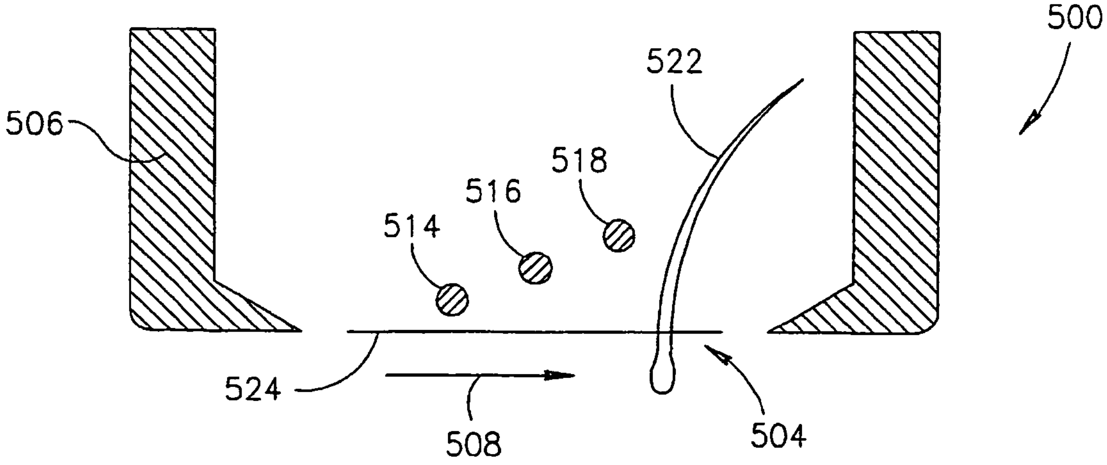
FIG. 4B is a cross sectional view of an alternative hair cutting apparatus, in accordance with an exemplary embodiment of the invention.

FIG. 4B shows an alternative exemplary embodiment of hair cutting apparatus 500' comprising heat elements 514', 516' and 518' that are of different heights in respect a skin surface 524 direction beneath slot 504' in housing 506'. Heat elements 514', 516' and 518' are positioned so that as apparatus 500' moves in direction 508, they sequentially cut a hair 522' at different levels in relation to skin surface 524.

Heat element 518', for example, cuts hair 522' at two millimeters above skin surface 524, though it could be positioned to cut hair 518' at one millimeter or less or 10 millimeters or more above skin 524.

Following heat element 518', heat element 516', for example, cuts hair 522 to a lower level in relation to skin surface 524, for example one millimeter, though it could be positioned to cut hair 528 at as little as 0.5 millimeters or less as long as 5 millimeters or more.

Following heat element 516', heat element 514' cuts hair 522, for example, so it is flush with skin surface 524, though heat element 514' could be set to cut hair 522 at 0.5 millimeters or greater. Alternatively or additionally, when heat element 516' is positioned flush with skin surface 524, it is capable of cutting hair 522 below skin surface 524 due to the fact that heat from heat element 514' spreads along shaft of hair 522, below skin surface 524'.

For example, heat element 514' could cut hair 522 to 0.5 millimeters below skin surface 524 or even one millimeter or more below skin surface 524, depending, for example, on the magnitude of heat generated and/or duration of contact between heat element 514' and skin surface 524. Other factors affecting the depth to which hair 522 is cut below skin surface 524 include, for example, hair 522 shaft thickness and/or number of hairs 522 contacting heat element 514' simultaneously, thereby dissipating the peak heat from heat element 514' and diminishing its cutting power.

In an alternative embodiment of the present invention, heat elements 514', 516' and 518' (and/or elements 514, 516, 518) provide pulsed heat. The pulsing of the heat can be simultaneous for heat elements 514' 516' and/or 518'. Alternatively or additionally, the pulsing of heat from heat elements 514', 516' and 518' may not be simultaneous, allowing lower peak power requirements for apparatus 500' during operation.

A bottom 512 (FIG. 4A) of housing 506 can be of a variety of shapes that provide, for instance, comfort to skin 524 and/or ease of use. For instance, bottom 512 could be curved with a single curve or with multiple curves.

Figure 6:
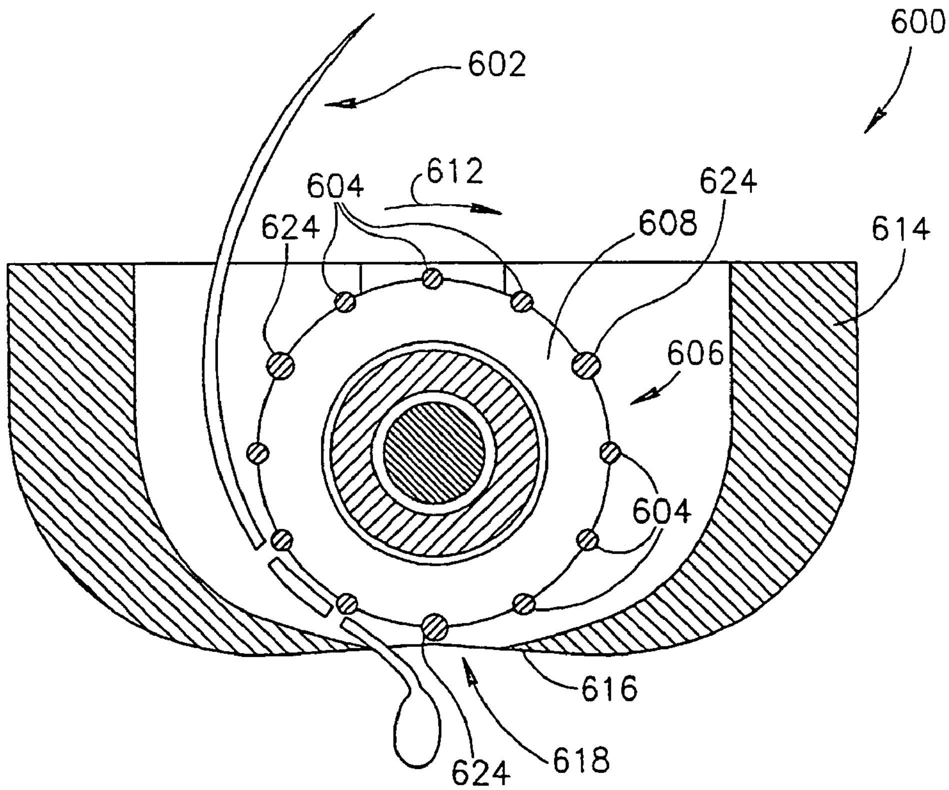
FIGS. 6 and 7 are cross-sectional and top perspective views, respectively, of an embodiment of a hair cutting device, in accordance with an exemplary embodiment of the invention.
Figure 7:
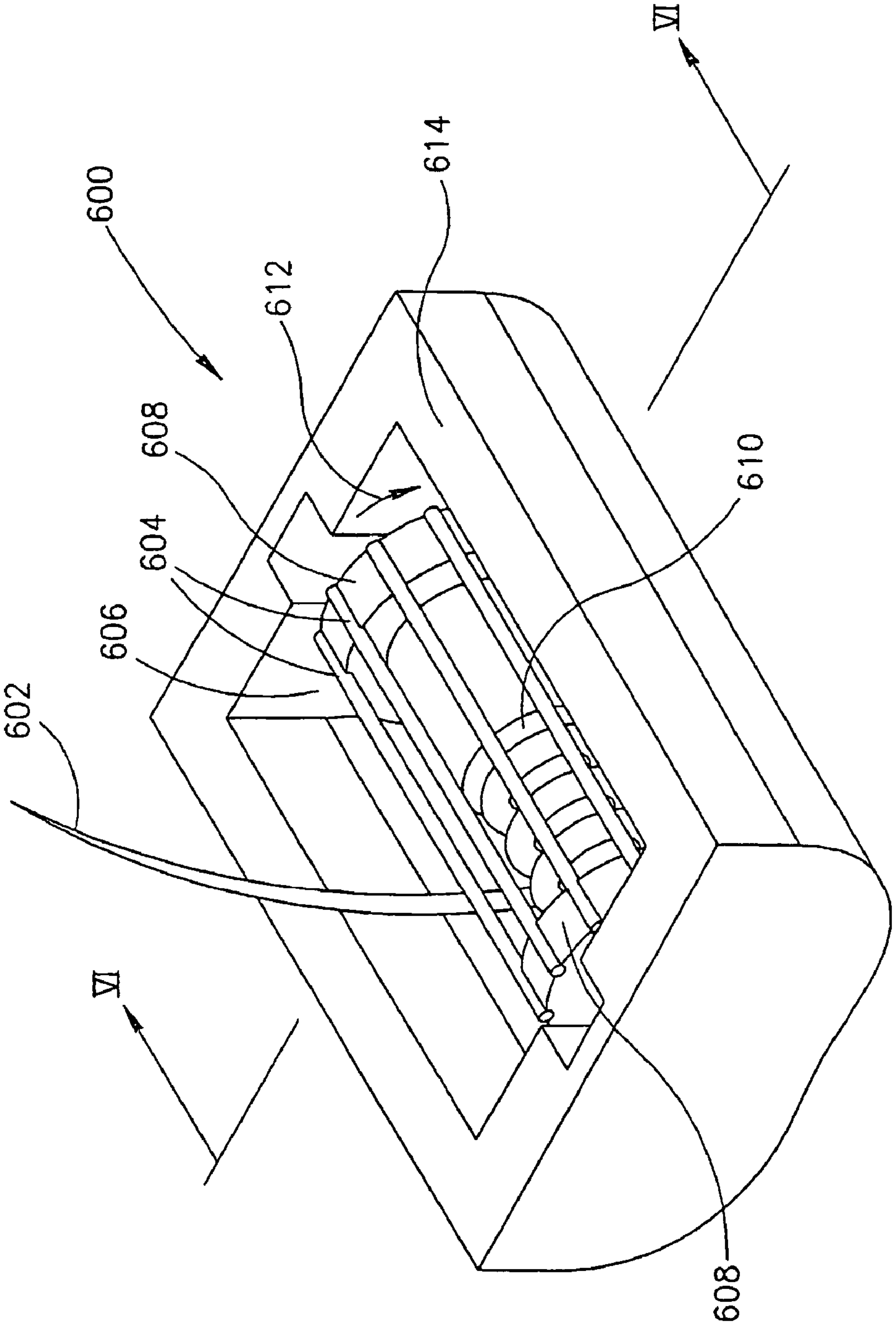

FIGS. 6 and 7 are cross-sectional and top perspective views of an embodiment of a hair cutting device 600, cutting a hair 602, according to an embodiment of the present invention. A plurality of heat elements 604 (shown as round wires) are shown on a cylinder 606. Heat elements 604 are attached to two end plates 608, which are urged apart by a spring 610, keeping heat elements 604 taught in spite of expansion during heating.

A motor (not shown) mechanically rotates a cylinder 606 that supports heat elements 604 in a direction 612 during the hair cutting process. Hair cutting device 600 preferably includes a housing 614 shown in cross-section in FIG. 6. A surface 616 of housing 614 contacts the skin. Hair 602, for example enters housing 614 through a slot 618, contacts heat elements 604 and are cut.

Slot 618, for example, is between a few millimeters to 1 cm or more wide, depending on the amount of hair 602 desired to be cut on each pass. It should be noted that heat elements 604 may be in contact with the skin while cutting hair 602. However, since heat elements 604 move along the skin surface as cylinder 608 rotates, heat elements 604 are not in any one place for a long enough time to cause damage to the skin. Pulsed or continuous heat may be generated from heat elements 602 in this embodiment.

For simplicity, in this and the other embodiments, the location of the power supply and any commutation required to transfer electricity to heat elements 604 is not shown. However, a simple commutator arrangement may be used to electrify end plates 608 and continuously electrify heat elements 604. Alternatively, end plates 608 are non-conducting and heat elements 604 have their ends connected to a common rotating connection. Alternatively, heat elements 604 are heated only just before they reach slot 618 and the electricity is disconnected from them after they leave the vicinity of slot 618.

While slot 618 is shown as being open, in some embodiments of the invention, a thin screen is provided over slot 618 through which hairs pass. A screen, for example that is non-heat conducting, comprises a series of slits or a mesh. Even with such a screen, heat elements 604 may be kept in effective contact with the skin surface.

Optionally, in addition to one or more heat elements 604 of one cross sectional size or thickness, an embodiment of hair cutting device 600 includes heat elements 624 of more than one cross-sectional size or thickness.

In an exemplary embodiment, heat elements 604 of different cross sectional sizes are situated on different portions of cylinder 606 so that thicker heat element 624 cuts hair 602 that, for example, is resistant to cutting by heat element 604.

Figure 8:
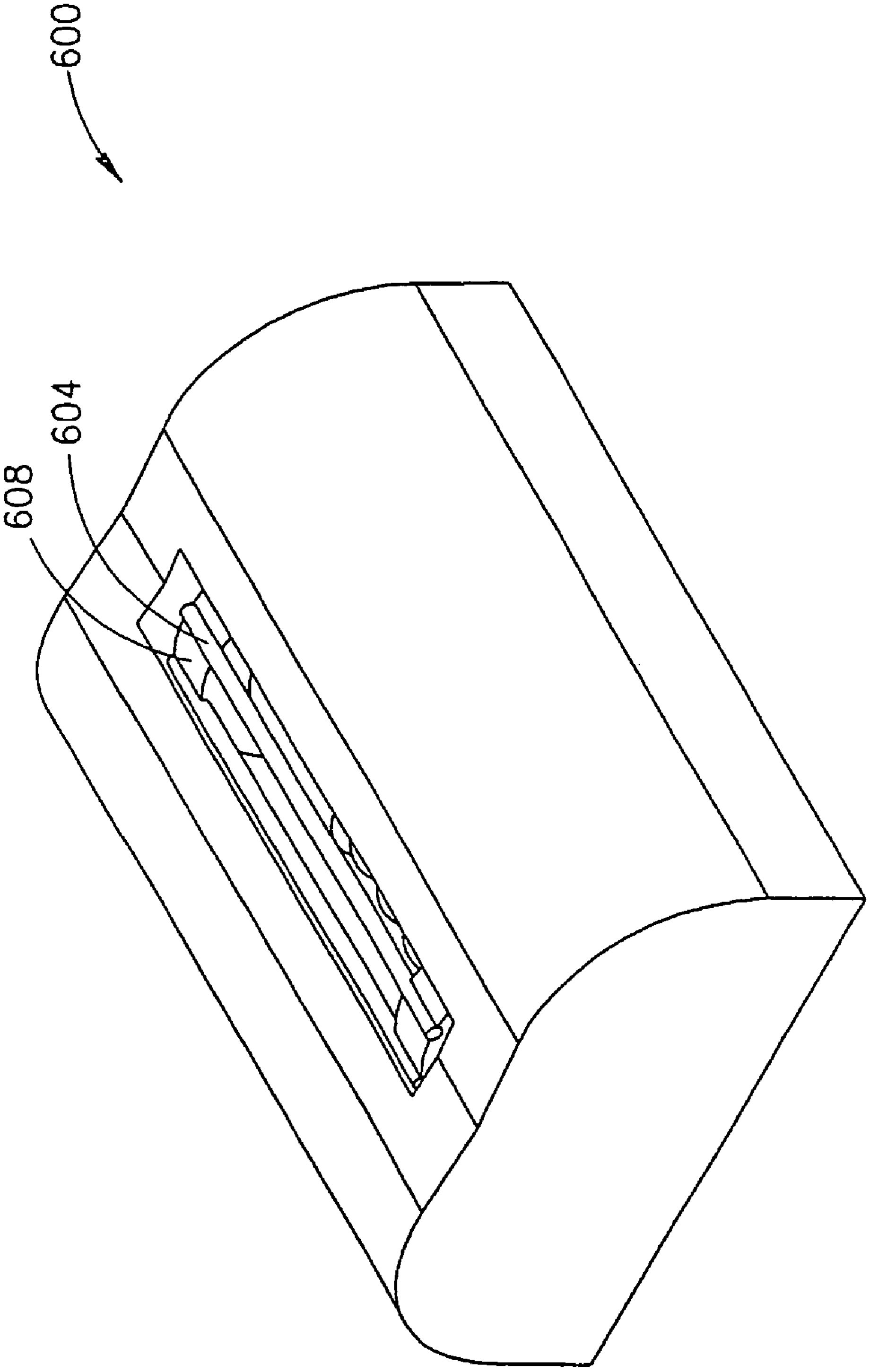
FIG. 8 is a bottom perspective view of the device of FIGS. 6 and 7, in accordance with an exemplary embodiment of the invention.

FIG. 8 shows a bottom perspective view of device 600 in FIGS. 6 and 7, in accordance with an exemplary embodiment of the invention.

Figure 9A:
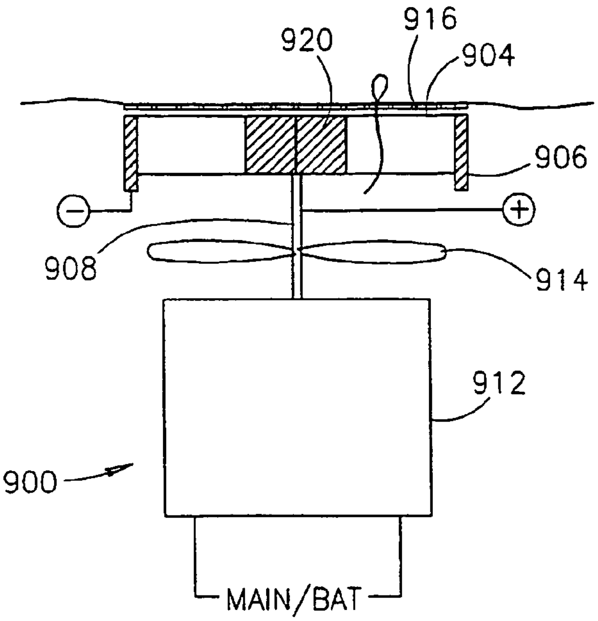
FIGS. 9A–C is respective partial side, end and perspective views of an alternative motorized example of a hair cutting apparatus, in accordance with an exemplary embodiment of the invention.
Figure 9B:
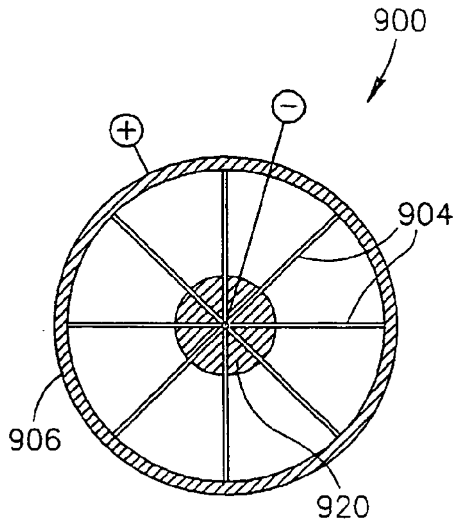
Figure 9C:
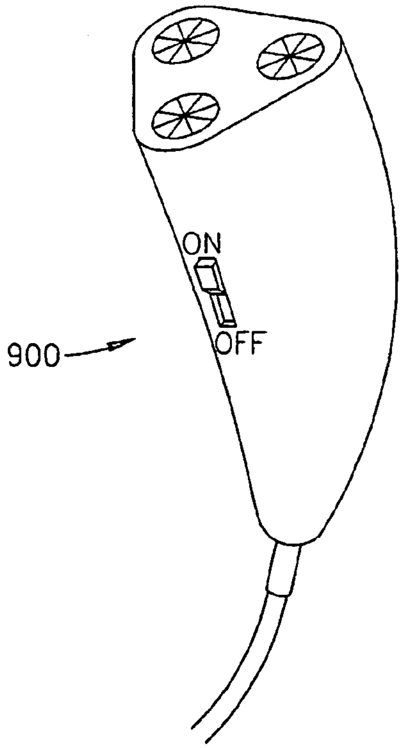

FIGS. 9A–C show respective cross-sectional partial side, cross-sectional end and perspective views of an alternative motorized example of a hair cutting apparatus 900, in accordance with an exemplary embodiment of the present invention. In this embodiment, a plurality of heat elements 904 are mounted between a hub 920 and an outer ring 906. Hub 920 is formed with a shaft 908, which is rotated during operation by a motor 912, which also turns an optional fan, 914. Alternatively, two motors are provided, one that rotates hub 920 and a second motor that turn fan 914.

As motor 912 turns, heat elements 904 pass across slots or holes in a faceplate 916, through which hairs enter the device. The faceplate may be formed with radial or circumferential slots or with openings of round or square shape. The same variations in heating cycles, and electric power described with respect to FIGS. 6–8 are available for this embodiment. FIG. 9C is a possible external view of a hair cutting apparatus embodiment, in accordance with an exemplary embodiment of the invention.

Figure 10A:
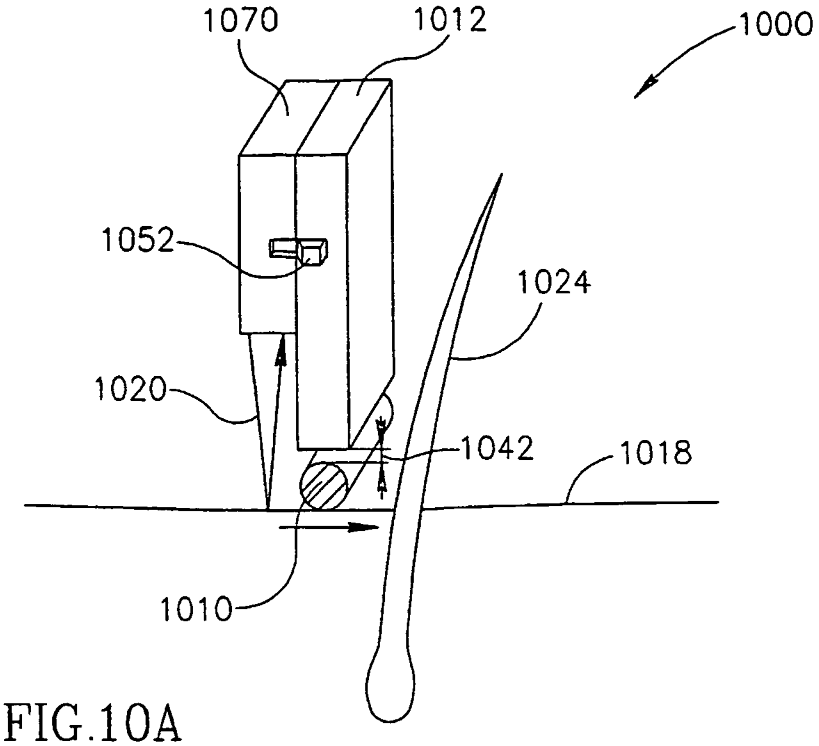
FIG. 10A is a heat generator with an optical velocity detector, in accordance with an exemplary embodiment of the invention.
Figure 10B:
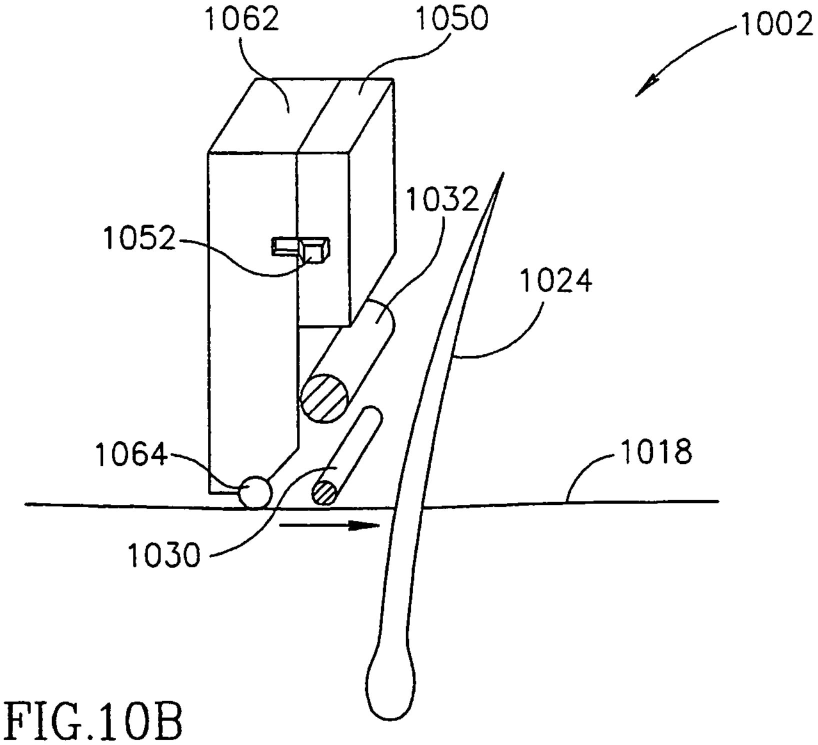
FIG. 10B is a heat generator with a servo-velocity detector, in accordance with an exemplary embodiment of the invention.

FIGS. 10A and 10B are schematic representations of hair cutting apparati 1000 and 1002, equipped with detectors 1070 and 1062 respectively that measure motion and/or velocity, in accordance with an exemplary embodiment of the invention. In apparatus 1000, optical motion/velocity detector 1070 is shown while in apparatus 10B, mechanical motion/velocity detector 1062 is shown. Both units 1000 and 1002 provide either pulsed or continuous current that is changed in relation to the motion and/or velocity.

FIG. 10A shows hair cutting apparatus 1000 with a cross section of a wire heat element 1010 that heats with either pulsed or non-pulsed heat, in accordance with an exemplary embodiment of the invention. A base 1012 regulates the power from a power supply (not shown) to heat element 1010 according to information provided by detector 1070.

A distance 1042 between wire heat element 1010 and base 1012, for example, is 30 microns. Additionally or alternatively, distance 1042 is generally 10 microns or less or 40 microns to 0.1 millimeters or more, dependent, for example, upon the flexibility of wire 1010. For example, when heat element 1010 comprises a flexible material, distance 1042 can be greater than, for example, when heat element 1010 comprises a hard material that does not bend as much.

In an exemplary embodiment, when detector 1070 is configured as a velocity detector, velocity is detected through an optical wave 1020 that reflects from skin 1018 or, for example, a hair 1024. Velocity detector 1070 can use a variety of methods for determining velocity along a portion of skin 1018. For instance, an optical wave 1020 can be used to register Doppler shift to determine velocity of unit 1000. When unit 1000 ceases movement, or moves below a minimal velocity, current to wire heat element 1010 is shut off. Additionally or alternatively, unit 1000 contains a manual switch that can be operated by a user.

Alternatively, detector 1070 can be configured as a motion detector that switches on current to wire heat element 1010 so that it heats only when there is a minimal movement of hair cutting apparatus 1000 in relation to skin surface 1016.

Optionally, heat element 1010, for example, produces a continuous current and the level of current is varied in relationship to velocity as detected by detector 1070. When heat element 1010 moves at a lower speed, for example 20–30 millimeters per second, current is provided to heat element 1010, for example at 0.5 to one ampere. When the speed of heat element 1010 increases to 30–40 millimeters per second, current is provided to heat element 1010, for example, from 1 to 1.3 amperes. Above 40 millimeters per second, the level of 1 to 1.3 amperes, for example, is maintained. These figures relating to peak current and/or duty cycle are used, for example, when heat element 1010 is made nickel chromium with a length of 20 millimeters and a diameter of 70 microns and can vary based upon changes in diameter, length and/or material.

FIG. 10B shows a hair cutting apparatus 1002 with cross sections of heat elements 1030 and 1032 (supported by a base 1050) that provide heat to cut hair 1024, in accordance with an exemplary embodiment of the invention. Unit has a mechanical velocity detector 1062 that uses a mechanical wheel 1064 to determine velocity or motion in relation to skin surface 1018.

Alternatively, a mechanical ball can be used in place of mechanical wheel 1064, similar to those used in a computer mouse that rolls on skin surface 1018. As in detector 1070 of unit 1000, detector 1062 of unit 1002 functions to detect motion whereby current to heat elements 1030 and 1032 ceases below a specific amount of motion. Additionally or alternatively, detector 1062 functions to detect variations in velocity, thereby varying temperature, pulsation rate and/or width in heat elements 1030 and/or 1032.

Optionally, both heat elements 1030 and 1032 have the same cross section and one or more of the temperature, pulse width and or pulse repetition is changed to both heat elements 1030 and 1032 in response to changes in speed of unit 1002.

Additionally or alternatively, heat element 1030 is heated to full capacity while heat element 1032 is not heated or, optionally, heated below its maximal heat capacity. When velocity of unit 1002 is slowed, for example, velocity detector 1062 detects the change in speed and signals base 1050. Base 1050 decreases the temperature of heat element 1030 and/or increases the temperature of heat element 1032. As heat element 1032 is of a greater offset from skin 1018, it cuts hair 1024 without causing damage to skin 1018.

Additionally or alternatively, base 1050 increases the pulse width or the pulse repetition of heat element 1032 to cut hair 1024 at a lower velocity along skin 1018.

Either motion detector and/or velocity detector 1070 can be configured with units 1000 and/or 1002, including any of the various embodiments of either unit noted above. To understand the workings of motion detector and/or velocity detector 1070, reference is now made to FIGS. 14–18.

Figure 14:
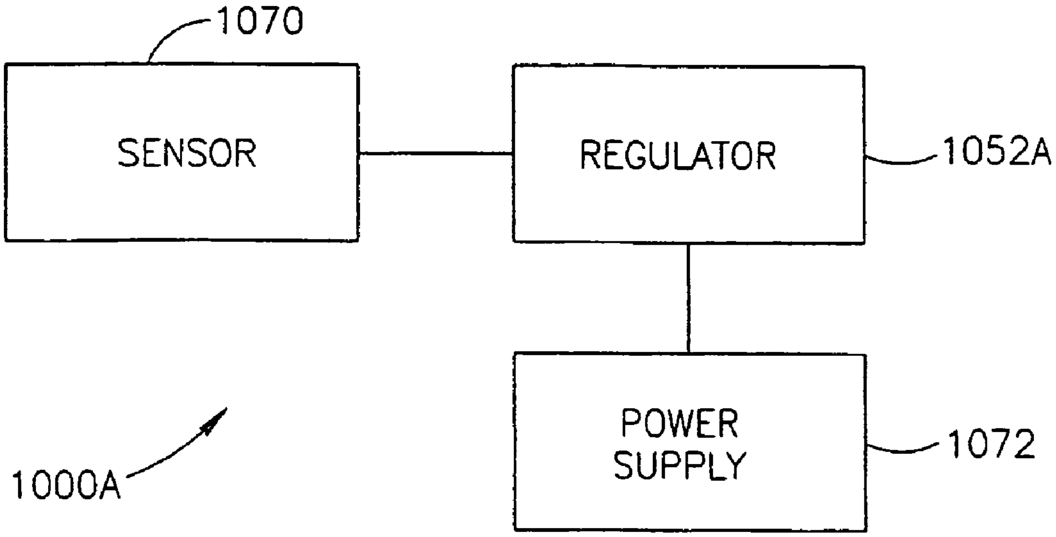
FIG. 14 is an electrical functional block diagram of a section of a hair cutting apparatus, in accordance with an exemplary embodiment of the invention.

FIG. 14 is an electrical functional block diagram of a section 1000A of optical hair cutting apparatus 1000 including detector 1070, power regulating base 1012 and its associated power, in accordance with an exemplary embodiment of the invention. Optical mouse sensor 1070 detects velocity of unit 1000 and signals a regulator 1052A to regulate power from a power supply 1072. Alternatively, a mechanical mouse sensor 1062 is utilized in place of optical sensor 1070.

Figure 15:
FIG. 15 is an electrical schematic diagram of pulses from an optical mouse velocity detector on a hair cutting apparatus, in accordance with an exemplary embodiment of the invention.

FIG. 15 is an electrical schematic diagram 1072 (not shown to scale) of pulses from power supply as a result of regulation by regulator 1052A, in accordance with an exemplary embodiment of the invention. As the velocity of apparatus 1000 or 1002 is at a given level, pulsing from power supply 1072 appears in an area 1502. Alternatively, as the velocity of apparatus 1000 or 1002 increases, pulsing from power supply 1072 appears in an area 1504. More frequent pulses with the same pulse width, for example, result in a higher peak temperature.

Figure 16:
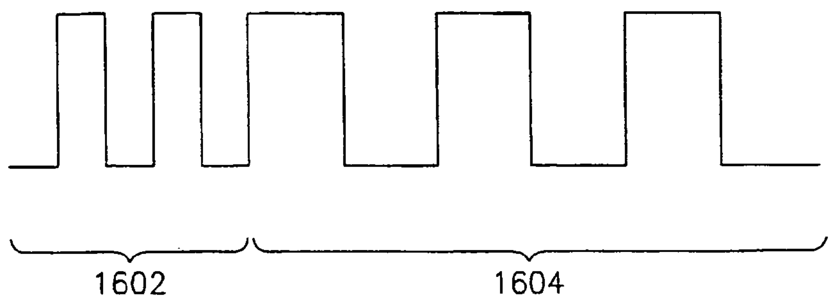
FIG. 16 is an electrical schematic diagram of pulses from an electronic circuit on a hair cutting apparatus, in accordance with an exemplary embodiment of the invention.

FIG. 16 is a diagram of pulses from regulator 1052A on hair cutting apparatus 1000 equipped with velocity detector 1070 or hair cutting apparatus equipped with velocity detector 1062, in accordance with an embodiment of the present invention. A high repetition rate of pulses 1602 occurs when apparatus 1000 or 1002 moves rapidly in relation to a hair 1024 (FIG. 10A). A low repetition rate of pulses 1604 occur when apparatus 1000 or 1002 moves slowly in relation to hair 1024. Both pulses 1604 and 1602 have the same duty cycle.

Additionally or alternatively, detectors 1070 and 1062 of units 1000 and 1002 respectively, may function as motion detectors, providing heat only when a specific minimum speed is reached. Illustrations of detectors 1070 and 1062 in embodiments as motion detectors are provided in FIGS. 17 and 18.

Figure 17:
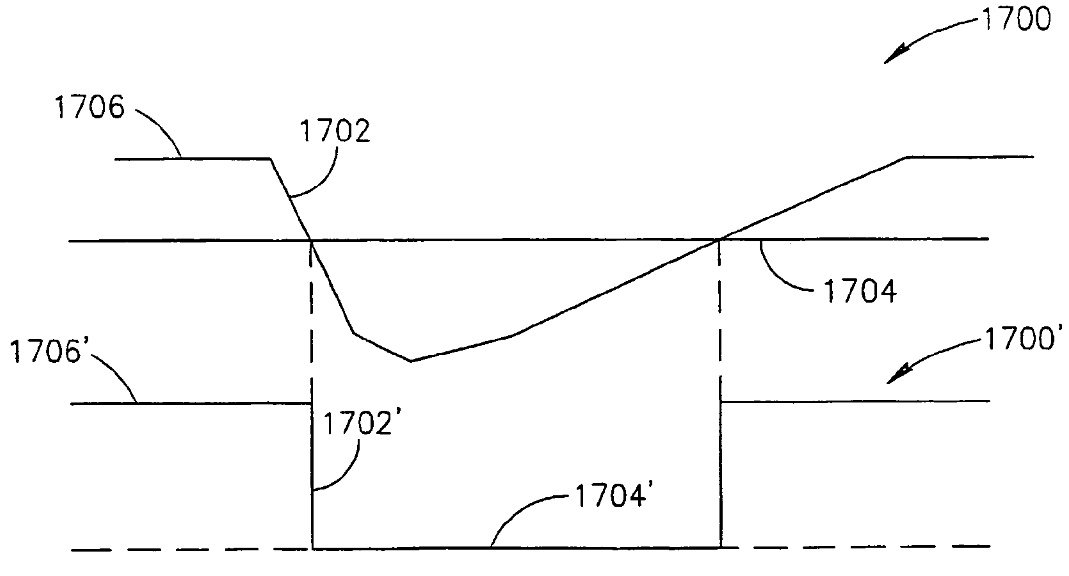
FIG. 17 is an electrical schematic diagram of voltage in response to a motion detector on a hair cutting apparatus, in accordance with an exemplary embodiment of the invention.

FIG. 17 is an electrical schematic diagram of a DC voltage 1706' in response to a speed of motion 1706, in accordance with an exemplary embodiment of the invention. Speed of motion 1706, for example is sensed by motion detector 1070 (FIG. 10A) while DC voltage 1706' is controlled by regulator 1052A on hair cutting apparatus 1000.

A falling speed of motion 1702 (as sensed by sensor 1070) that falls below a base level 1704, causes DC voltage 1706' to fall shut off a voltage level 1704'.

Figure 11A:
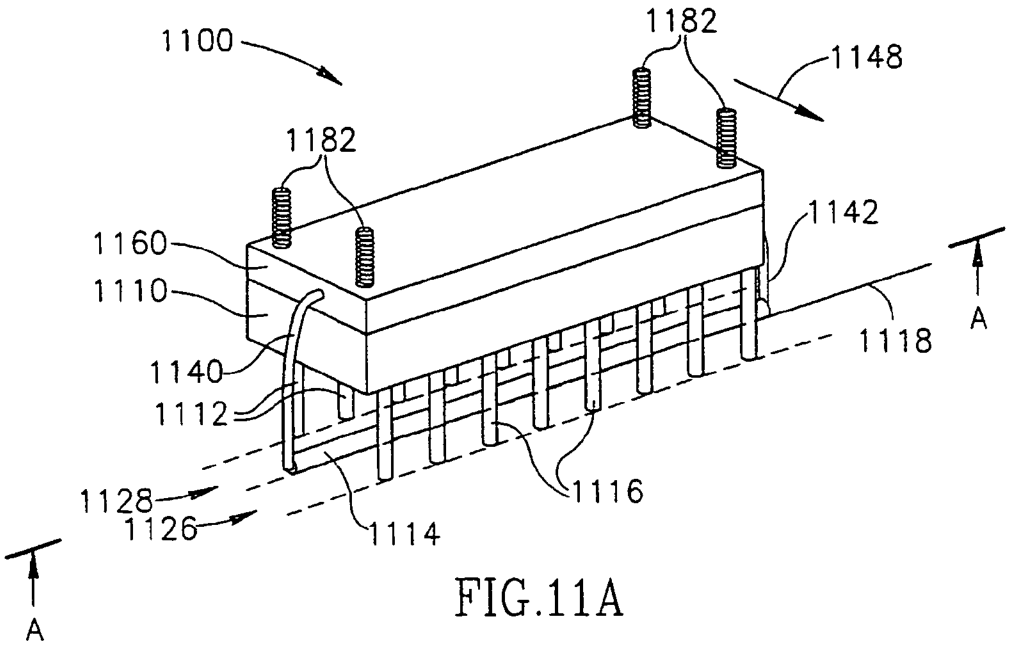
FIG. 11A is a hair cutting apparatus with a heat element situated between two parallel lines of skin depressors, in accordance with an exemplary embodiment of the invention.

FIG. 11A is a hair cutting apparatus 1100 with a heat element 1114 situated between a first line of skin depressors 1112 parallel to a second line of skin depressors 1116 that are attached to a base 1110, in accordance with an exemplary embodiment of the invention. Base 1110 can be made of clear material, for example a clear plastic that maintains the passage of an optical sensor signal through base 1110. Additionally or alternatively, base 1110 is made of one or more materials, including opaque materials, for example a ceramic or opaque plastic, and the path of an optical sensor signal is set to bypass the opaque areas. Additionally or alternatively, there is no optical sensor signal and heat element 1114 provides pulsed heat that, for example, does not require optical sensing.

When base 1110 is made of a clear plastic or an alternative optical path is provided, an optical velocity detector 1160 mounted above it sends optical signals to skin surface 1018 that return to velocity detector 1160 that registers velocity and maintains heat element 1114 in a heated state. In an embodiment shown in FIG. 11E, as explained below, for example, neither velocity detector 1160 or pulsed current are required to prevent damage to skin 1018 while being touched by heat element 1114.

When optical signals traveling through base 1110 register that hair cutting apparatus 1100 is not in motion in relation to a skin surface 1018, velocity detector 1160 switches off the current to heat element 1114 so that heat element 1114 cools, preventing damage to skin surface 1018. A delay in motion for 100 ms, for example, signals base 1110 to make necessary changes in temperature. Alternative periods of motion delay can be used, for example, with different peak temperatures and/or pulse rates in heat element 1114.

Heat element 1114, for example, is attached to a tension generator 1140 at one end and/or a tension generator 1142 at its opposite end. Tension generators 1140 and/or 1142 serve to keep heat element 1114 taught during motion across skin surface 1118. Though tension generators 1140 and 1142 are, for example, flexible strips that serve to provide tension on heat element 1114, they could have a variety of other configurations. For example, tension generators 1140 and 1142 could comprise two coiled springs that provide tension on heat element 1114.

Heat element 1114 optionally has a diameter of 0.070 millimeters, though it could have a diameter of 0.02 or less or 0.5 millimeters or more based upon a variety of factors such as materials, temperature and/or pulsation rate. Skin depressors 1112 and 1116, for example, have a diameter of 3 millimeters though they could be 5 millimeters or thicker or 1 millimeter or thinner, depending, for example on the desired strength of depressors 1112 and/or 1116 and/or the ease with which they are to travel along skin 1118.

Skin depressors 1112 and 1116 are shown as being straight comb-like pieces though their shape could vary. For instance, skin depressors 1112 and 1116 could be curved along their length. Alternatively or additionally, the tips of skin depressors 1112 and 1116 that contact skin surface 1118 could be any shape, for example ending in round balls to provide smooth movement along skin 1118. Alternatively or additionally, depressors 1112 and/or 1116 can be coated, for example with a ceramic or Teflon coating, to aid in smoother movement along skin 1118.

A distance 1126 of heat element 1114, for example, to row of skin depressors 1112 usually equal to a distance 1128 to row of skin depressors 1116. Distances 1126 and 1128, for example, are one millimeter though they could be 1.5–5 millimeters or more or 0.8–0.2 millimeters or less, depending on the diameter, peak temperature and/or duty cycle of heat element 1114.

Figure 11B:
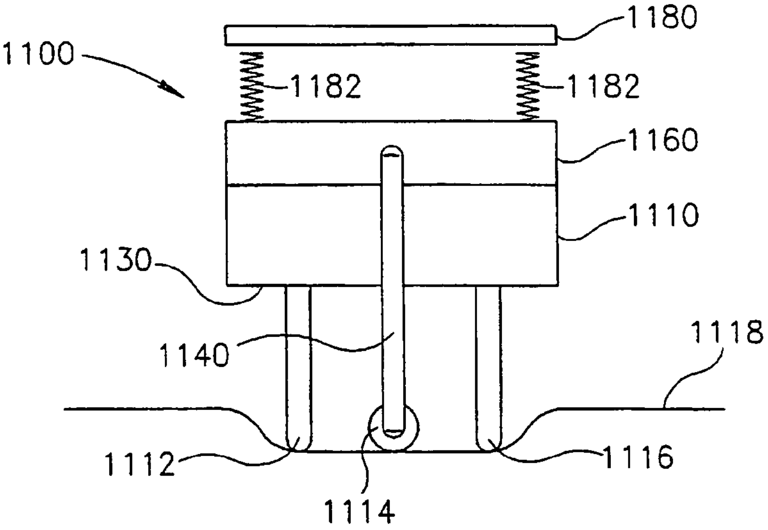
FIG. 11B is a side view schematic diagram of a hair cutting apparatus shown in FIG. 11A on a skin surface, in accordance with an exemplary embodiment of the invention.
Figure 11C:
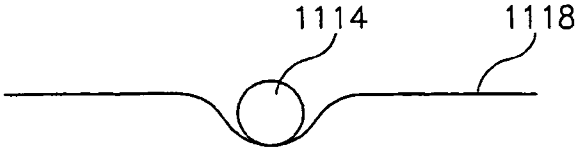
FIG. 11C is a schematic diagram of a heat element on a skin surface.

In FIG. 11B, skin depressors 1112 and 1116 maintain skin surface 1118 flat so that heating heat element 1114 does not sink into skin surface 1118, thereby providing greater surface contact and associated heat buildup that can damage skin surface 1118, in accordance with an exemplary embodiment of the invention. Heat element 1114 is shown in FIG. 11C on skin surface 1118 without skin depressors 1112 and 1116, demonstrating that it sinks into skin surface 1118, potentially causing skin damage due to the increased contact area with skin surface 1118.

The length of skin depressors 1112 and 1116, for example, is 2 millimeters, though they could be 1–0.5 millimeters or shorter or 3–8 millimeters or longer, based for example, on the distance heat element 1114 is spaced from an edge 1130 that is, for example, parallel to a skin surface 1118.

In an alternative embodiment, skin depressors 1116 are of a first length and skin depressors 1112 are of a second, different, length that puts base 1110 at an angle to skin surface 1118, for example between 30 and 60 degrees. The variation in angle of base 1110, for example, may be determined by the most frequent use for which unit 1100 is built, such as home or professional use. A profession using unit 1100 on others may prefer a different angle than, for example, a home user cutting his or her own hair.

Optionally, skin depressors 1112 are parallel to skin depressors 1116 and heat element 1114 is parallel to skin depressors 1112. Additionally or alternatively, skin depressors 1112 are parallel to skin depressors 1116 and heat element 1114 is not parallel to skin depressors 1112.

Additionally or alternatively, skin depressors 1112 are not parallel to skin depressors 1116 and heat element 1114 is parallel to skin depressors 1112 or skin depressors 1116. Alternatively, skin depressors 1112 are not parallel to skin depressors 1116 and heat element 1114 is not parallel to skin depressors 1112 or skin depressors 1116.

Alternatively or additionally, skin depressors 1112 and 1116 are removable from hair cutting apparatus 1100 and supplied in multiple lengths, widths or shapes based upon texture, plushness or length of hair 1024 (FIG. 10B) to be cut.

In an embodiment of the present invention, apparatus 1100 contains springs 1182 and a handle 1180 (shown schematically) that an operator can grasp during use of unit 1100. Springs 1182 provide shock absorption between heat element 1114 and skin 1118. Additionally or alternatively, springs 1182 allow unit 1100 to follow contours in skin surface 1118 during movement along skin 1118 by an operator. While springs 1182 are shown in each corner of handle 1180, as few as one spring, for example, in the middle of handle 1180 or many more springs 1182, for example 10 or more, can be located on apparatus 1100. A greater amount of springs 1182 may be built into units that are, for example, for use with sensitive skin. Fewer springs 1182 may be built into units that are for example, for use with more robust skin.

Figure 11D:
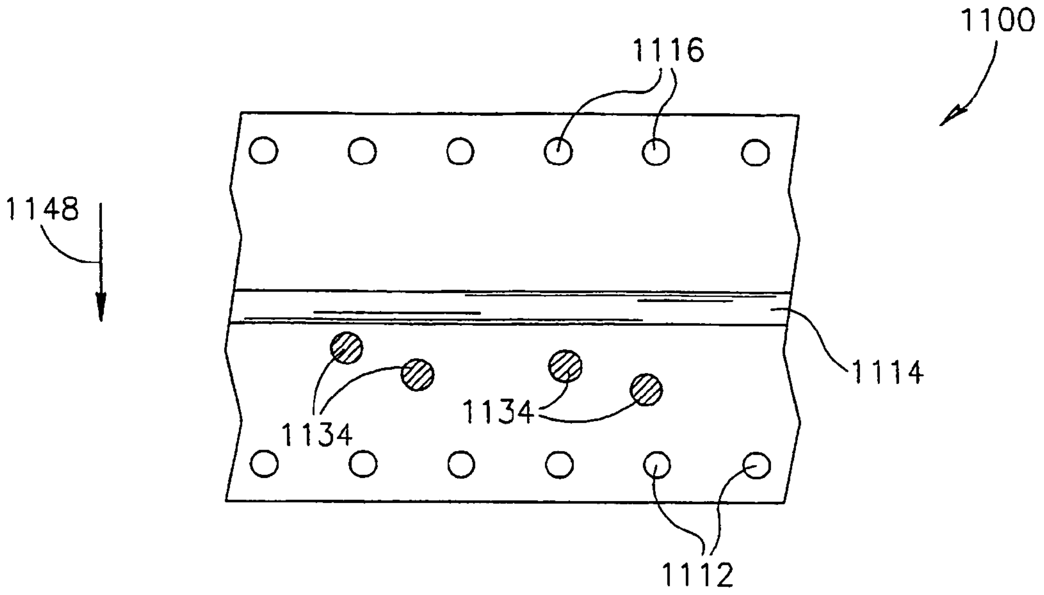
FIG. 11D is a portion of a hair cutting apparatus of FIG. 11A taken along lines A—A, in accordance with an exemplary embodiment of the invention.

FIG. 11D shows a portion of a hair cutting apparatus 1100 taken along a line A—A with heat element 1114 situated between skin depressors 1112 that are parallel to skin depressors 1116, in accordance with an exemplary embodiment of the invention. Hair cutting apparatus 1100 moves in a direction 1148 and hairs 1134, shown in cross section, are cut by heat element 1114.

Figure 11E:
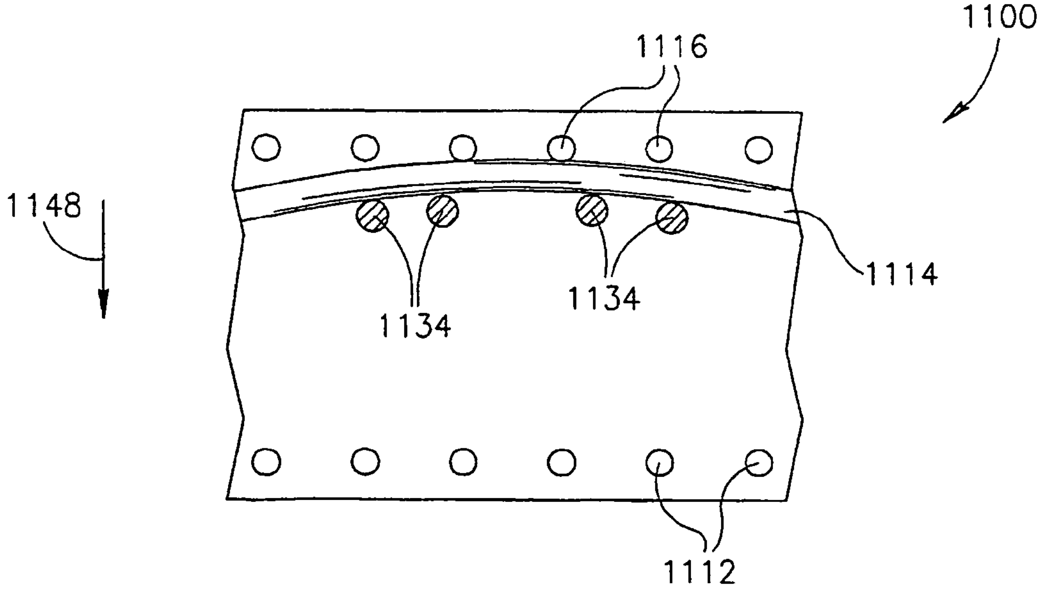
FIG. 11E is a portion of a hair cutting apparatus of FIG. 11A taken along lines A—A, in accordance with an exemplary embodiment of the invention at a different time.

FIG. 11E shows a portion of a hair cutting apparatus 1100 taken along lines A—A with a portion of heat element 1114 displaced by the pressure of hairs 1134, shown in cross section, as unit 1100 is moved in a direction 1148, in accordance with an exemplary embodiment of the invention. Heat element 1114 is flexible, as noted earlier, by virtue of being attached to tension generators 1140 and 1142 (shown in FIG. 11A). Heat element 1114 cools as it touches skin depressors 1116, preventing heat buildup in heat element 1114 that can damage skin surface 1118. As heat element 1114 cools, it passes over some of hairs 1134 without cutting them.

Hair cutting apparatus 1100 is passed again, in direction 1148 for example, to cut the balance of hairs 1134 that were not cut during the first pass. In each pass over hairs 1134, some of hairs 1134 are cut. When pressure on heat element 1114 builds, heat element 1114 bends and touches skin depressors 1112 or 1116 and cools. With heat element 1114 cooled, it passes over the balance of hairs 1134 without cutting them. Another pass with hair cutting apparatus 1100 is then made in order to cut the remainder of hairs 1134.

Alternatively, apparatus 1100 comprises a safety feature that prevents heat element 1114 from heating when apparatus 1100 is not in motion in relation to hairs 1134. In and exemplary embodiment, heat element 1114 is charged with a potential electric current while skin depressors 1112 and/or 1116 are connected to an electrical ground. When apparatus is not being moved in relation to hairs 1134, heat element 1114 does not touch skin depressors 1112 and/or 1116 and therefore current does not pass through heat element 1114 (FIG. 11D). When not in motion, heat element 1114, for example, remains cool.

As apparatus 1100 is moved in direction 1148, heat element 1114 touches hair 1134, causing it to bend and touch skin depressors 1116 (FIG. 11E). With heat element 1114 touching skin depressors 1116, current flows from electrically charge heat element 1114 through electrically grounded skin depressors 1116. Grounded heat element 1114 heats up and cuts hairs 1134. Upon cessation of motions, heat element 1114 no longer touches skin depressors 1112 and/or 1116 (FIG. 11D) and heat element 1114 cools once again.

In an alternative embodiment, skin depressors 1112 and/or 1116 are charged with a potential electric current while heat element 1114 is connected to an electrical ground. Movement of apparatus 1100 in relation to hairs 1134 in direction 1148, causes heat element 1114 to touch skin depressors 1116, thereby completing an electrical circuit, causing heat element 1114 to heat up. Alternatively or additionally, apparatus 1000 is moved in the opposite direction and heat element touches skin depressors 1112 and heats up.

Figure 12:
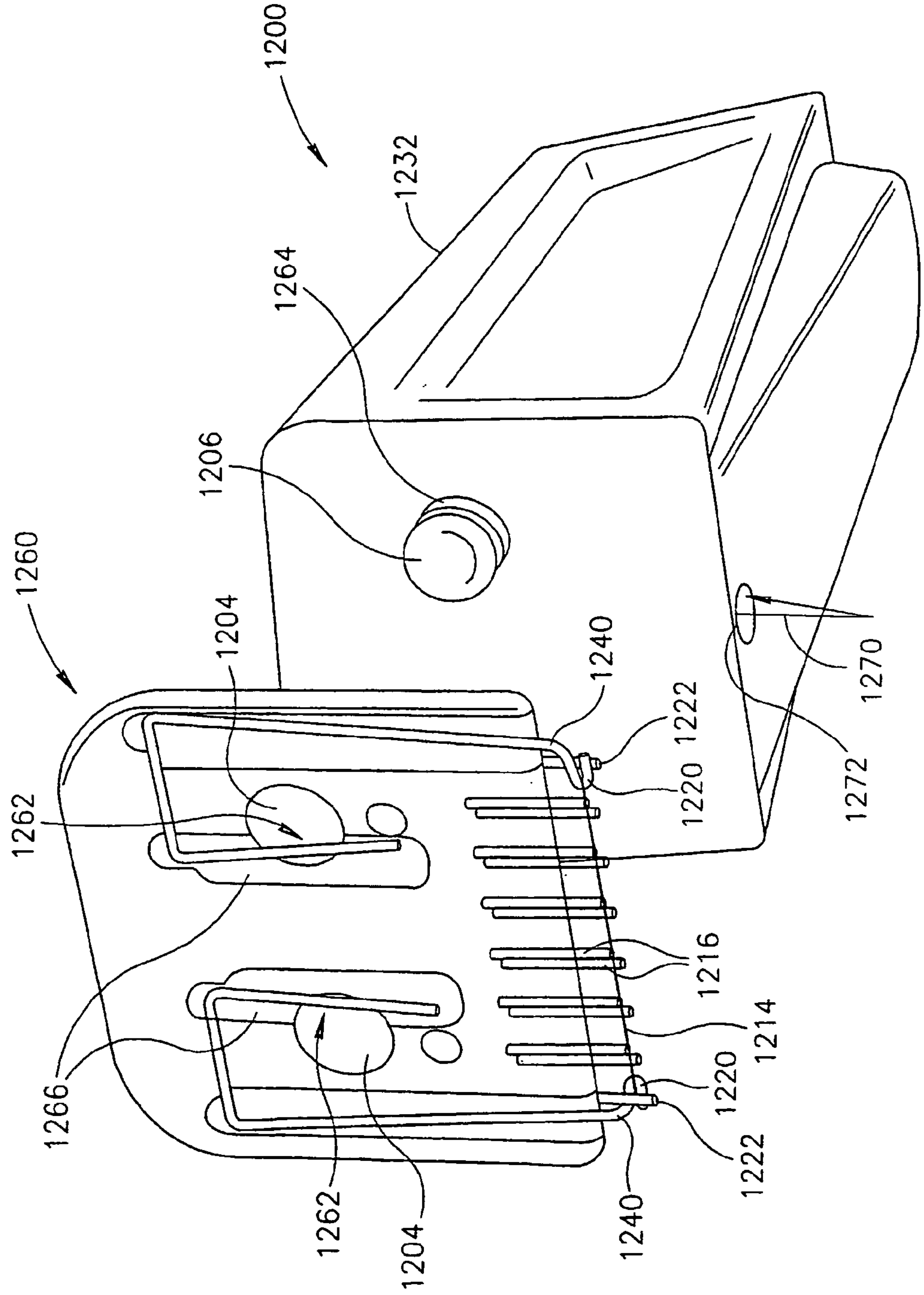
FIG. 12 is a partially exploded view of a hair cutting unit, in accordance with an exemplary embodiment of the invention.
Figure 13:
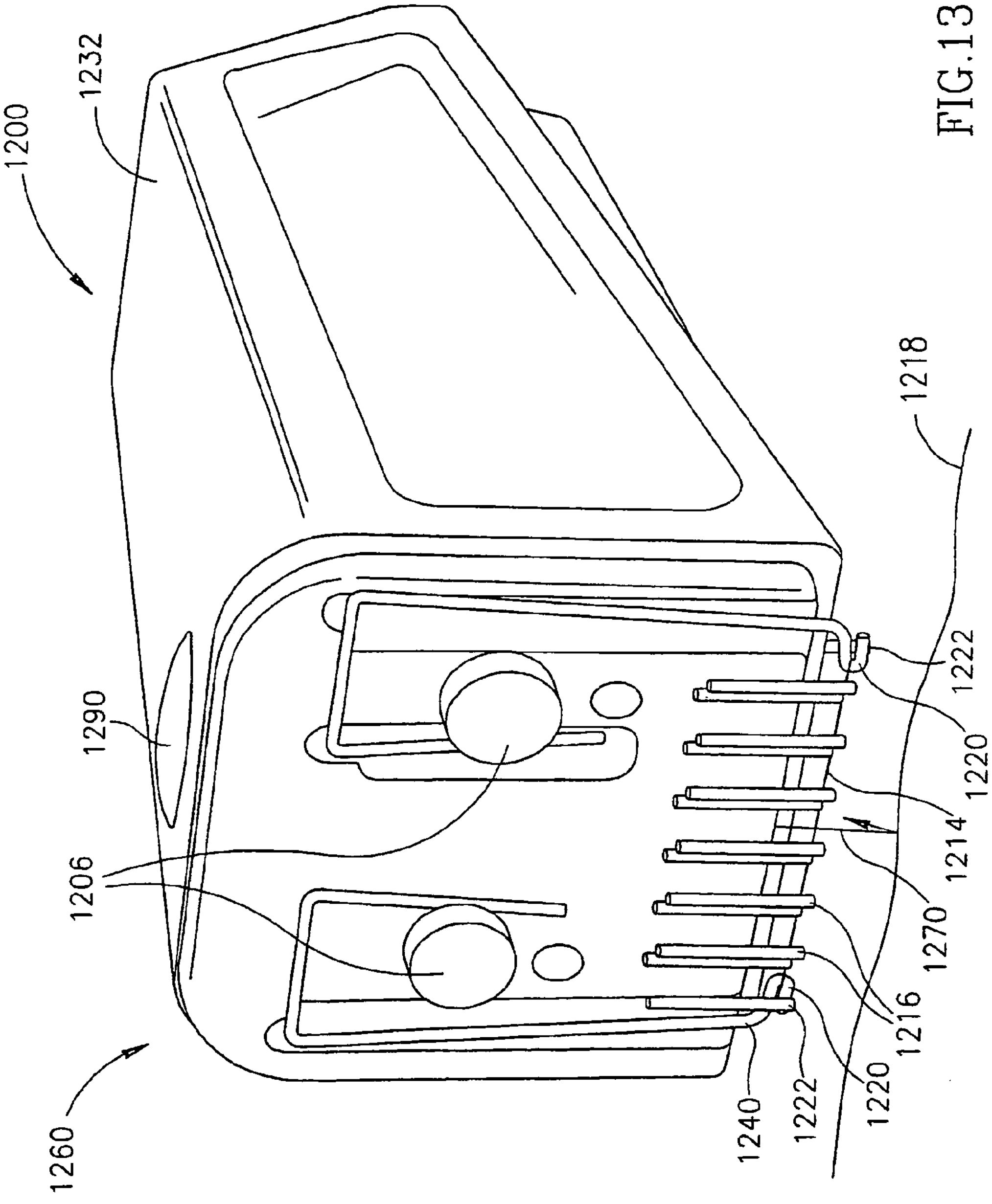
FIG. 13 is an assembled hair cutting unit corresponding to the exploded view of FIG. 12, in accordance with an exemplary embodiment of the invention.

FIGS. 12 and 13 show a hair cutting apparatus 1200 with a grasper 1232 that is suitable for grasping by the hand of an operator, in accordance with an exemplary embodiment of the invention. A frame 1260, including a heat element 1214, is shown removed from grasper 1232 in FIG. 12. In some embodiments of the present invention, frame 1260 includes one or more tension generators 1240 attached to one or more heat elements 1214 to tighten them as they deform upon pressing against hair during hair cutting or expand due to heat application.

Frame 1260, for example, is attached to grasper 1232 so that frame 1260 is held at a specific angle to skin 1218, for example perpendicular to skin 1218. The connection of frame 1260 to grasper 1232, for example is by one or more posts 1206 that may be, for example, flexible or spring loaded and fit into post connection 1204. As frame 1260 moves across the contour of skin 1218, it moves up and down and/or swivels on flexible posts 1206 in relation to grasper 1232. Additionally or alternatively, one or more flexible posts 1206 between frame 1260 and grasper 1232 absorb shock caused by tremors and shakes as grasper 1232 is held in an operator's hand. The flexibility of posts 1206 prevents heat element 1214 from pressing with undue force into a skin surface 1218, causing skin damage.

In an exemplary embodiment, posts 1206 are comprised of a metal contact area 1264 that provides electric current to contact area 1262 of tension generator 1240. Contact area 1262 contacts a metal contact 1262 when it is pushed through a posthole 1204 as frame 1260 snaps onto posts 1206. Contact area 1262 is, for example, springy and set in a contact gutter 1266 that is wide to allow movement of contact area 1262 as contact area 1262 snaps into place.

Additionally or alternatively, contact area 1262 is springy to allow movement of frame 1260 on posts 1206 in post holes 1204 while frame 1260 moves in relation to grasper 1232 without disrupting power between posts 1206 and contact area 1262. For example, area 1264 is wider than contact area 1262, allowing movement between frame 1260 and grasper 1232. Additionally or alternatively, posts 1206 swivel to provide flexibility to frame 1260.

Optionally, frame 1260 comprises two rows of skin depressors 1216 that are perpendicular to an area of skin 1218 (FIG. 13) and, for example, parallel to one or more heat elements 1214. When frame 1260 comprises two rows of skin depressors 1216, one or more heat elements 1214 are optionally between them, as shown.

Optionally, skin depressors 1216 include a mechanism for preventing skin damage due to the protrusion of a tension generator end 1220. For example, a skin depressor 1222 located near tension generator end 1220 is longer than tension generator end 1220 preventing its contact and resultant heat damage to skin 1218. In an alternative embodiment, skin depressors 1222 do not protrude beyond tension generator end 1220, and tension generator end 1220 is coated with a material that insulates it so that build-up of heat is below a level that causes skin damage.

A velocity detector beam 1270 is shown in relation to an optical velocity detector 1272 that senses the speed of unit 1200 along skin 1218 and thereby varies the electric pulse width, repetition rate and/or temperature of heat element 1214 to prevent skin damage.

FIG. 13 is an assembled unit 1200, with a perspective showing an operator controlled on-off switch 1290, in accordance with an exemplary embodiment of the invention.

While the invention has been described with respect to a limited number of embodiments, it will be appreciated that many variations, modifications and other applications of the invention may be made. For example, while either pulsed or continuous heating has been described in reference to an embodiment of the invention, pulsed heating is generally usable in all the embodiments that were described with continuous heating. Further, embodiments that were described as using pulsed heating can use continuous heating if means for avoiding overheating of the skin as described herein are provided.

Also, combination of heat elements from variations may be combined and single heat elements may be used. As an example, one or more heat elements that displace and, in one embodiment, cool as they touch skin depressors, may be utilized in an embodiment utilizing a cylindrical arrangement of heat elements. Such variations and modifications, as well as others that may become apparent to those skilled in the art are intended to be included within the scope of the invention, as defined by the appended claims.

A variety of values have been utilized to describe the heat elements comprising the invention including, diameters, lengths and materials of heat elements, pulse rates, pulse widths, current levels and peak temperatures through heat elements. Additionally, a variety of values have been utilized to describe structures besides heat elements, including length, diameter and position of skin depressors in relation to heat elements and the minimum velocity or motion at which a controller signal a heat element to provide heat. Although a variety of values for these, and other, structures have been provided, it should be understood that these values could vary even further based upon a variety of engineering principles, materials, intended use and designs incorporated into the invention.

The terms "include", "comprise" and "have" and their conjugates as used herein mean "including but not necessarily limited to."

It will be appreciated by a person skilled in the art that the present invention is not limited by what has thus far been described. Rather, the scope of the present invention is limited only by the following claims.

The invention claimed is:

1. A hair cutting apparatus comprising:

a structure, a portion of which being adapted for placement against a skin surface where hair is to be cut;

a heat generator comprising one or more heat elements positioned to touch said hair and heated to a temperature sufficient to cut hair, at least one of said heat elements being juxtaposed with said portion; and a controller that controls the power source to provide pulsed heating of said one or more heat elements such that the heat elements do not burn said skin surface.

2. Apparatus according to claim 1 wherein the one or more heat elements are heated for a period of between 10 and 100 msec for each on-off cycle.

3. Apparatus according to claim 1 wherein the heating of the heat element is repeated at a pulse repetition rate of 1–100 Hz.

4. Apparatus according to claim 1 wherein said controller comprises a velocity detector.

5. Apparatus according to claim 4 wherein the velocity detector causes said heat generator to increase its rate of repeated pulsing when the velocity of said apparatus increases in relation to said skin; and to decrease its rate of repeated pulsing when the velocity of said apparatus decreases in relation to said skin.

6. Apparatus according to claim 4 wherein the velocity detector causes said heat generator to increase the width of each pulsation during said repeated pulsing when the velocity of said apparatus increases in relation to said skin; and to decrease the width of each pulsation during said repeated pulsing when the velocity of said apparatus decreases in relation to said skin.

7. Apparatus according to claim 4 wherein said pulsation changes to continuous heating when the velocity increases above a specific rate, as sensed by said velocity detector.

8. Apparatus according to claim 4 wherein the velocity detector causes said heat generator to increase the temperature of said heat element when the velocity of said apparatus increases in relation to said skin; and to decrease the temperature of said heat element when the velocity of said apparatus decreases in relation to said skin.

9. Apparatus according to claim 4 wherein said velocity detector comprises an optical velocity detector.

10. Apparatus according to claim 4 wherein said velocity detector comprises a mechanical velocity detector.

11. Apparatus according to claim 1 wherein the heat generator includes an interruptible power supply that energizes said heat element, said controller controls the interruptible power supply to periodically heat said heat generator to a temperature at which it is hot enough to cut hair and then causes it to cool to a lower temperature at which said skin surface is not damaged.

12. Apparatus according to claim 11 wherein said controller comprises a motion detector.

13. Apparatus according to claim 12 wherein the motion detector controls said heat generator, switching said heat generator on when said heat generator is in motion in relation to said skin and switching said heat generator off when said heat generator is not in motion in relation to said skin.

14. Apparatus according to claim 13 wherein said motion detector comprises an optical motion detector.

15. Apparatus according to claim 13 wherein said motion detector comprises a mechanical motion detector.

16. Apparatus according to claim 1 wherein the one or more heat elements comprise ribbon-shaped elements and a wide side of said ribbon-shaped elements is substantially perpendicular to said skin.

17. Apparatus according to claim 1 wherein the one or more heat elements comprise a wire substantially parallel to said skin.

18. Apparatus according to claim 1 wherein the one or more heat elements comprise two or more heat elements.

19. Apparatus according to claim 18 wherein a plane formed by the two or more heat elements is parallel to said skin.

20. Apparatus according to claim 18 wherein the plane formed by the two or more heat elements is perpendicular to said skin.

21. Apparatus according to claim 18 wherein the plane formed by the two or more heat elements is neither parallel nor perpendicular to said skin.

22. Apparatus according to claim 18 wherein the two or more heat elements have different cross-sectional areas.

23. Apparatus according to claim 18 wherein the two or more heat elements have different cross-sectional configurations.

24. Apparatus according to claim 18 wherein heat applied by at least two of the two or more heat elements is applied at a different pulse rate.

25. Apparatus according to claim 18 wherein heat applied by at least two of the two or more heat elements is applied at a different pulse width.

26. Apparatus according to claim 18 wherein the temperature in at least two of the two or more heat elements is different.

27. Apparatus according to claim 1 wherein at least one end of one heat element is attached to a tension generator.

28. Apparatus according to claim 27 wherein the tension generator comprises a spring.

29. Apparatus according to claim 27 wherein the tension generator comprises a spring-loaded wire.

30. Apparatus according to claim 1 wherein said portion that is adapted for placement against said skin comprises two or more skin depressors that contact said skin surface.

31. Apparatus according to claim 30 wherein said two or more skin depressors are perpendicular to said skin.

32. Apparatus according to claim 30 wherein said two or more skin depressors comprise one or more rows of skin depressing elements.

33. Apparatus according to claim 30 wherein said two or more skin depressors comprise at least two rows of skin depressing elements.

34. Apparatus according to claim 33 wherein said two or more skin depressors comprise parallel rows of skin depressing elements.

35. Apparatus according to claim 33 wherein said one or more heat elements are located between said two rows of skin depressing elements.

36. Apparatus according to claim 32 wherein said one or more heat element is parallel to one or more rows of skin depressing elements.

37. Apparatus according to claim 32 wherein said one or more heat element is not parallel to one or more rows of skin depressing elements.

38. Apparatus according to claim 33 wherein said at least one or more heat element is not parallel to said two or more rows of skin depressing elements.

39. Apparatus according to claim 32 wherein at least one end of one heat element is connected to a tension generator and one or more of said skin depressing elements protrude beyond said tension generator.

40. Apparatus according to claim 30 wherein when the at least one heat element is so constructed that when it contacts one or more hairs during motion, it displaces opposite its direction of motion in relation to the skin.

41. Apparatus according to claim 40 wherein when said heat element displaces in an amount sufficient to contact one of said skin depressors, it cools as it contacts the skin depressors.

42. Apparatus according to claim 40 wherein when said heat element displaces in an amount sufficient to contact one of said skin depressors, it heats as it contacts the skin depressors.

43. Apparatus according to claim 1 wherein said portion adapted for placement against a skin surface is separate from said structure and said portion is mounted with one or more mountings on said structure.

44. Apparatus according to claim 43 wherein said mounting comprises flexible rubber posts.

45. Apparatus according to claim 43 wherein said mounting comprises spring loaded mountings.

46. Apparatus according to claim 43 wherein said mountings are electrically connected to said heat elements.

47. Apparatus according to claim 1 wherein the controller comprises a motor that moves the heat elements along the skin, so that the temperature of the skin does not rise to a level that causes it to burn.

48. Apparatus according to claim 47 wherein the heat elements are elongate heat elements arranged to form a discontinuous cylindrical surface having a rotation axis.

49. Apparatus according to claim 48 wherein as the heat elements rotate about the axis they are periodically brought into contact with and removed from contacting said skin surface.

50. Apparatus according to claim 47 wherein the axes of the heat elements radiate from an axis, said axis being perpendicular to the axes of the heat elements.

51. Apparatus according to claim 48 wherein the controller rotates the elongate heat elements about the axis.

52. Apparatus according to claim 1 and including a fan that provides cooling for the heat element.

53. Apparatus according to claim 1 wherein said one or more elements contact said skin surface.

54. A method of cutting hair comprising:

pulsing a heat element touching the skin, said heat element being heated to a peak temperature high enough to cause the cutting of hair without burning of skin at said position; wherein said pulsation allows the heat element to cool between pulses to an extent that it does not burn the skin while still cutting hair.

55. A method according to claim 54 and including changing the pulsing dependent on the velocity of the heat element with respect to the skin to assure that it does not burn the skin wherein said changing comprises changing the pulsing rate of pulsated heat to the heat element.

56. A method according to claim 54 and including changing the pulsing dependent on the velocity of the heat element with respect to the skin to assure that it does not burn the skin wherein said changing comprises changing the width of each pulse of pulsated heat to the heat element.

57. A method according to claim 54 and including changing the pulsing dependent on the velocity of the heat element with respect to the skin to assure that it does not burn the skin wherein said changing comprises changing the temperature of each pulse of heat to the heat element.

58. A method according to claim 54 and including changing the pulsing dependent on the velocity of the heat element with respect to the skin to assure that it does not burn the skin wherein said changing is accomplished by a velocity detector when it detects a change in velocity of said heat element in relation to said skin.

59. A hair cutting apparatus comprising:

a structure, a portion of which being adapted for placement against a skin surface where hair is to be cut;

a heat generator comprising one or more heat elements positioned to touch said hair and heated to a temperature sufficient to cut hair, at least one of said heat elements being juxtaposed with said portion; and a controller that controls the power source to provide pulsed heating of said one or more heat elements, the controller further comprising a velocity detector.

* * * * *

UNITED STATES PATENT AND TRADEMARK OFFICE

CERTIFICATE OF CORRECTION

PATENT NO. : 7,170,034 B2
APPLICATION NO. : 10/363365
DATED : January 30, 2007
INVENTOR(S) : Pinchas Shalev et al.

It is certified that error appears in the above-identified patent and that said Letters Patent is hereby corrected as shown below:

Claim 54, at Column 23, Line 6, change “pulsation” to --pulsing--.

Signed and Sealed this

Sixth Day of November, 2007

JON W. DUDAS

*Director of the United States Patent and Trademark Office*